(12) United States Patent
Tiberg et al.

(10) Patent No.: US 11,135,215 B2
(45) Date of Patent: *Oct. 5, 2021

(54) OPIOID FORMULATIONS

(71) Applicant: Camurus AB, Lund (SE)

(72) Inventors: Fredrik Tiberg, Lund (SE); Ian Harwigsson, Lund (SE); Markus Johnsson, Lund (SE)

(73) Assignee: Camurus AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/142,723

(22) Filed: Jan. 6, 2021

(65) Prior Publication Data

US 2021/0177833 A1 Jun. 17, 2021

Related U.S. Application Data

(60) Continuation of application No. 16/882,186, filed on May 22, 2020, now Pat. No. 10,912,772, which is a
(Continued)

(51) Int. Cl.
*A61K 31/4748* (2006.01)
*A61K 31/485* (2006.01)
(Continued)

(52) U.S. Cl.
CPC ........ *A61K 31/4748* (2013.01); *A61K 9/0024* (2013.01); *A61K 31/485* (2013.01);
(Continued)

(58) Field of Classification Search
CPC .. A61K 31/4748; A61K 31/485; A61K 47/10; A61K 47/24; A61K 47/34; A61K 9/0024; A61K 47/14
See application file for complete search history.

(56) References Cited

U.S. PATENT DOCUMENTS 3,433,791 A 3/1969 Bentley
4,582,835 A 4/1986 Lewis et al.
(Continued)

FOREIGN PATENT DOCUMENTS

CN 101014319 A 8/2007
EP 0767656 A1 4/1997
(Continued)

OTHER PUBLICATIONS

The Advantages & Challenges of Developing A Drug Product in Prefilled Syringes: retrieved from internet: https://pdfs.semanticscholar.org/2c62/53e37fab1ca0c165527a8bb1f18dc5bdfd11.pdf. Retrieved on Mar. 23, 2021.*
(Continued)

*Primary Examiner* — Hong Yu
(74) *Attorney, Agent, or Firm* — Choate, Hall & Stewart LLP; Charles E. Lyon; Michael A. Shinall

(57) ABSTRACT

A depot precursor formulation comprising:
  a) a controlled-release matrix;
  b) at least oxygen containing organic solvent;
  c) at least 12% by weight of at least one active agent selected from buprenorphine and salts thereof, calculated as buprenorphine free base. Corresponding depot compositions and methods of treatment in pain management, by opioid maintenance and related methods are provided.

30 Claims, 10 Drawing Sheets

Related U.S. Application Data division of application No. 15/866,043, filed on Jan. 9, 2018, now abandoned, which is a division of application No. 14/416,421, filed as application No. PCT/EP2013/065855 on Jul. 26, 2013, now Pat. No. 9,937,164, which is a continuation-in-part of application No. 13/558,463, filed on Jul. 26, 2012, now abandoned.

(60) Provisional application No. 61/806,185, filed on Mar. 28, 2013.

(51) Int. Cl.
| | |
|---|---|
| A61K 47/10 | (2017.01) |
| A61K 47/24 | (2006.01) |
| A61K 47/34 | (2017.01) |
| A61K 9/00 | (2006.01) |
| A61K 47/14 | (2017.01) |

(52) U.S. Cl.
CPC .............. *A61K 47/10* (2013.01); *A61K 47/14* (2013.01); *A61K 47/24* (2013.01); *A61K 47/34* (2013.01)

(56) References Cited

U.S. PATENT DOCUMENTS

| | | | |
|---|---|---|---|
| 4,610,868 | A | 9/1986 | Fountain et al. |
| 4,938,763 | A | 7/1990 | Dunn et al. |
| 5,480,656 | A | 1/1996 | Okada et al. |
| 5,648,096 | A | 7/1997 | Gander et al. |
| 5,759,563 | A | 6/1998 | Yewey et al. |
| 5,807,573 | A | 9/1998 | Ljusberg-Wahren et al. |
| 5,955,502 | A | 9/1999 | Hansen et al. |
| 5,958,379 | A | 9/1999 | Regenold et al. |
| 6,071,524 | A | 6/2000 | Ribier et al. |
| 6,113,943 | A | 9/2000 | Okada et al. |
| 6,132,766 | A | 10/2000 | Sankaram et al. |
| 6,455,066 | B1 | 9/2002 | Fischer et al. |
| 6,464,987 | B1 | 10/2002 | Fanara et al. |
| 6,495,164 | B1 | 12/2002 | Ramstack et al. |
| 6,599,517 | B1 | 7/2003 | Ljusberg-Wahren et al. |
| 6,630,115 | B1 | 10/2003 | Kaneeda et al. |
| 6,630,155 | B1 | 10/2003 | Chandrashekar et al. |
| 6,656,385 | B2 | 12/2003 | Lynch et al. |
| 6,660,278 | B1 | 12/2003 | Larsson et al. |
| 8,097,239 | B2 | 1/2012 | Johnsson et al. |
| 8,236,292 | B2 | 8/2012 | Thuresson et al. |
| 8,236,755 | B2 | 8/2012 | Thuresson et al. |
| 8,454,945 | B2 | 6/2013 | McCook et al. |
| 8,545,832 | B2 | 10/2013 | Thuresson et al. |
| 8,546,326 | B2 | 10/2013 | Joabsson et al. |
| 8,920,782 | B2 | 12/2014 | Joabsson et al. |
| 8,921,387 | B2 | 12/2014 | Norton et al. |
| 8,975,270 | B2 | 3/2015 | Norton et al. |
| 9,168,251 | B2 | 10/2015 | Richardson et al. |
| 9,272,044 | B2 | 3/2016 | Norton et al. |
| 9,498,432 | B2 | 11/2016 | Norton et al. |
| 9,526,788 | B2 | 12/2016 | Johnsson et al. |
| 9,585,959 | B2* | 3/2017 | Tiberg .................. A61P 1/00 |
| 9,649,382 | B2 | 5/2017 | Joabsson et al. |
| 9,782,402 | B2 | 10/2017 | Norton et al. |
| 9,827,241 | B2 | 11/2017 | Norton et al. |
| 9,937,164 | B2 | 4/2018 | Tiberg et al. |
| 9,968,680 | B2 | 5/2018 | Joabsson et al. |
| 10,022,367 | B2 | 7/2018 | Zhou et al. |
| 10,198,218 | B2 | 2/2019 | Norton et al. |
| 10,558,394 | B2 | 2/2020 | Norton et al. |
| 10,587,864 | B2 | 3/2020 | Hayasaka et al. |
| 10,588,859 | B2 | 3/2020 | McCook et al. |
| 10,592,168 | B1 | 3/2020 | Norton et al. |
| 10,912,772 | B2* | 2/2021 | Tiberg .................. A61K 47/14 |
| 2002/0010127 | A1 | 1/2002 | Oshlack et al. |
| 2002/0065506 | A1 | 5/2002 | Gruber et al. |
| 2002/0182247 | A1 | 12/2002 | Maruo et al. |
| 2003/0003144 | A1 | 1/2003 | Keller |
| 2003/0044458 | A1 | 3/2003 | Wright et al. |
| 2004/0022820 | A1 | 2/2004 | Anderson |
| 2004/0033250 | A1 | 2/2004 | Patel et al. |
| 2004/0259899 | A1 | 12/2004 | Sanghvi et al. |
| 2005/0112188 | A1 | 5/2005 | Eliaz et al. |
| 2007/0265190 | A1 | 11/2007 | Thuresson et al. |
| 2007/0265329 | A1 | 11/2007 | Devang et al. |
| 2008/0124394 | A1 | 5/2008 | Johnsson et al. |
| 2008/0146490 | A1 | 6/2008 | Joabsson et al. |
| 2009/0155193 | A1 | 6/2009 | Joabsson et al. |
| 2009/0181068 | A1 | 7/2009 | Dunn |
| 2009/0264456 | A1* | 10/2009 | Sewell ............... A61K 31/4045 514/288 |
| 2010/0144754 | A1 | 6/2010 | Peltz et al. |
| 2011/0230569 | A1 | 9/2011 | Nistor et al. |
| 2013/0190341 | A1 | 7/2013 | Tiberg et al. |
| 2014/0162944 | A1 | 6/2014 | Tiberg et al. |
| 2014/0193347 | A1 | 7/2014 | Thuresson et al. |
| 2014/0275046 | A1 | 9/2014 | Ottoboni et al. |
| 2014/0323517 | A1 | 10/2014 | Whelan |
| 2014/0348903 | A1 | 11/2014 | Tiberg et al. |
| 2015/0064118 | A1 | 3/2015 | Thuresson et al. |
| 2015/0182522 | A1 | 7/2015 | Tiberg et al. |
| 2015/0359891 | A1 | 12/2015 | Chen et al. |
| 2018/0250286 | A1 | 9/2018 | Tiberg et al. |
| 2018/0256496 | A1 | 9/2018 | Tiberg et al. |
| 2020/0345719 | A1 | 11/2020 | Tiberg et al. |
| 2020/0375979 | A1 | 12/2020 | Tiberg et al. |
| 2021/0137916 | A1 | 5/2021 | Tiberg et al. |

FOREIGN PATENT DOCUMENTS

| | | |
|---|---|---|
| EP | 1848403 B1 | 3/2010 |
| WO | WO-95/13796 A1 | 5/1995 |
| WO | WO-1995/026715 A2 | 10/1995 |
| WO | WO-95/34287 A1 | 12/1995 |
| WO | WO-97/13528 A1 | 4/1997 |
| WO | WO-02/068562 A2 | 9/2002 |
| WO | WO-2005/046642 A1 | 5/2005 |
| WO | WO-2005/110360 A2 | 11/2005 |
| WO | WO-2005/117830 A1 | 12/2005 |
| WO | WO-2006/075125 A1 | 7/2006 |
| WO | WO-2010/020794 A1 | 2/2010 |
| WO | WO-2011/154724 A2 | 12/2011 |
| WO | WO-2012/160213 A1 | 11/2012 |
| WO | WO-2013/083459 A1 | 6/2013 |
| WO | WO-2013/083460 A1 | 6/2013 |
| WO | WO-2014/016428 A1 | 1/2014 |
| WO | WO-2014/047047 A1 | 3/2014 |
| WO | WO-2014/104784 A1 | 7/2014 |
| WO | WO-2014/130887 A1 | 8/2014 |
| WO | WO-2014/143839 A1 | 9/2014 |
| WO | WO-2016/066655 A1 | 5/2016 |
| WO | WO-2017/072059 A1 | 5/2017 |
| WO | WO-2020/077235 A1 | 4/2020 |

OTHER PUBLICATIONS

"Generic Lupron Depot Availability," Drugs.com, available at https://www.drugs.com/availability/generic-lupron-depot.html (last accessed Oct. 28, 2016). 4 pages.

"N-Methyl-2-pyrrolidone," *Wikipedia*, available at https://en.wikipedia.org/wiki/NMP (last accessed Jul. 7, 2016), 2 pages.

(+)-α-Tocopherol: retrieved from internet: http://www.sigmaaldrich.com/catalog/product/sigma/t3251?lang=en&region=US, retrieved on May 1, 2018.

Author Not Known, Implant: retrieved from internet: http://www.merriam-webster.com/dictionary/implant. Retrieved on Apr. 4, 2016.

Author Not Known, Skin anatomy: retrieved from internet: http://www.enchantedlearning.com/subjects/anatomy/skin/. Retrieved on Apr. 4, 2016.

Barauskas, J. et al., Bioadhesive lipid compositions: self-assembly structures, functionality, and medical applications, Mol Pharm, 11(3):895-903 (2014).

(56) References Cited

OTHER PUBLICATIONS

Das et al., Modification by Diacylglycerol of the Structure and Interaction of Various Phospholipid Bilayer Membranes, Biochemistry, 25(10):2882-2889 (1986).

European Medicines Agency, Information for the package leaflet regarding ethanol used as an excipient in medicinal products for human use, Committee for Medicinal Products for Human Use (CHMP), 35 pages (Sep. 20, 2018).

International Search Report for PCT/EP2016/072059 (Controlled-release formulations), issued by ISA/EP, 6 pages (dated Nov. 21, 2016).

International Search Report for PCT/GB2005/002217 (dated Oct. 19, 2005).

Lofwall, M. et al., Weekly and Monthly Subcutaneous Buprenorphine Depot Formulations vs Daily Sublingual Buprenorphine With Naloxone for Treatment of Opioid Use Disorder, JAMA Internal Medicine, pp. E1-E10 (2018).

Lupron Depot 7.5 mg: retrieved from internet: http://www.accessdata.fda.gov/drugsatfda_docs/label/2013/019732s040, 020517s035lbl.pdf. Retrieved on May 27, 2015.

Navari, Rudolph M., Overview of the updated antiemetic guidelines for chemotherapy-induced nausea and vomiting, Community Oncology, 4(4)(1):9 pages (2007).

NMP: retrieved from internet: https://www.google.com/search?q=nmp&sourceid=ie7&rls=com.microsoft:en-us:IE-SearchBox&ie=&oe=. Retrieved on Jan. 9, 2014.

Ottoboni, T. et al., Biochronomer technology and the development of APF530, a sustained release formulation of granisetron, Journal of Experimental Pharmacology, 6:15-21 (2014).

Tiberg, F. et al., "Chapter 16: Self-Assembling Lipid Formulations," *Long Acting Injections and Implants*, 315-333 (2012).

Written Opinion for PCT/EP2016/072059 (Controlled-release formulations), issued by ISA/EP, 9 pages (dated Nov. 21, 2016).

Larsson et al., Lipids: Structure, Physical Properties and Functionality, The Oily Press, Copyright, extract (2006).

Prescott, David M., Methods in cell biology, 14: 34 (1976).

Shah et al., Cubic phase gels as drug delivery systems, Advanced Drug Delivery Reviews, 47(2-3):229-250 (2001).

Tiberg et al., Drug Delivery Applications of Non-Lamellar Liquid Crystalline Phases and Nanoparticles, Journal of Drug Development Science & Technology, 21(1):101-109 (2011).

* cited by examiner

OPIOID FORMULATIONS

The present application is a continuation application of U.S. patent application Ser. No. 16/882,186, filed May 22, 2020 (now U.S. Pat. No. 10,912,772), which is a continuation application of U.S. Ser. No. 15/866,043, filed Jan. 9, 2018, which is a divisional application of U.S. patent application Ser. No. 14/416,421, filed Jan. 22, 2015 (now U.S. Pat. No. 9,937,164), which is a 371 national phase entry of PCT Application No. PCT/EP13/65855, filed Jul. 26, 2013, which claims priority to U.S. Provisional Application No. 61/806,185, filed Mar. 28, 2013, and to U.S. patent application Ser. No. 13/558,463, filed Jul. 26, 2012, each of which is hereby incorporated by reference in its entirety.

The present invention relates to formulation precursors (pre-formulations) for the in situ generation of controlled release opioid compositions. In particular, the invention relates to sustained release compositions and corresponding precursor formulations, containing at least one opioid bioactive agent, especially buprenorphine.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level, results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary. Furthermore, in some circumstances, such as in the fitting of implants (e.g. joint replacements or oral implants) the area of desired action may not remain accessible for repeated administration. Similarly, patient compliance may limit how regularly and/or how frequently administration can be made. In such cases a single administration must provide active agent at a therapeutic level over and extended period, and in some cases over the whole period during which activity is needed.

In the case of opioid active agents, the situation can be complex. Opioids administered for pain relief are given only to the extent needed because of the risk of dependence but effective pain management often requires at least a background level of stable administration. Furthermore, the administrative burden in supplying opioids is relatively high because of the danger of diversion for illicit use. The facility to provide a long-acting opioid administration for use in situations where pain relief for several days will inevitably be necessary (e.g. post operative pain relief, relief of cancer pain and/or relief of chronic pain such as chromic back pain) could therefore improve the experience for the patient and reduce the burden on the healthcare professionals.

The situation of administering opioids to people with any form of opioid dependence is even more complex. Opioids will often be prescribed to avoid or relieve the symptoms of withdrawal in those with an opioid dependence, but such subjects may have a lifestyle that makes daily dosing by a healthcare professional difficult. Patient compliance may therefore be a problem with such a regime. Some pharmaceuticals can be supplied to the patient for self-administration but the risk of diversion to illicit use is such that opioids are not typically supplied in this way. The dose required to provide a functional plasma concentration is relatively high in daily products and this makes the risk of diversion much higher.

Various methods have been used and proposed for the sustained release of biologically active agents. Such methods include slow-release, orally administered compositions, such as coated tablets, formulations designed for gradual absorption, such as transdermal patches, and slow-release implants such as "sticks" implanted under the skin.

One method by which the gradual release of a bioactive agent has been proposed is a so-called "depot" injection. In this method, a bioactive agent is formulated with carriers providing a gradual release of active agent over a period of a number of hours or days. These are often based upon a degrading matrix which gradually disperses in the body to release the active agent.

A controlled-release product, especially in ready-made-up form, which is administrable by simple injection offers a number of potential advantages, particularly in the treatment and management of opioid dependence. Such a product could be administered under the control of a healthcare worker to minimise risk of diversion but requires only a minimum imposition on that worker's time since the administration is infrequent (e.g. once a month). Ready-to-use products further do not require lengthy preparation.

The most common of the established methods of depot injection relies upon a polymeric depot system. This is typically a biodegradable polymer such poly (lactic acid) (PLA) and/or poly (lactic-co-glycolic acid) (PLGA) and may be in the form of a solution in an organic solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. Nos. 4,938,763, 5,480,656 and 6,113,943 and can result in delivery of active agents over a period of up to several months.

One alternative to the more established, polymer based, depot systems was proposed in U.S. Pat. No. 5,807,573. This proposes a lipid based system of a diacylglycerol, a phospolipid and optionally water, glycerol, ethylene glycol or propylene glycol to provide an administration system in the reversed micellar "$L_2$" phase or a cubic liquid crystalline phase. Since this depot system is formed from physiologically well tolerated diacyl glycerols and phospholipids, and does not produce the lactic acid or glycolic acid degradation products of the polymeric systems, there is less tendency for this system to produce inflammation at the injection site. The liquid crystalline phases are, however, of high viscosity and the $L_2$ phase may also be too viscous for ease of application. The authors of U.S. Pat. No. 5,807,573 also do not provide any in vivo assessment of the release profile of the formulation and thus it is uncertain whether or not a "burst" profile is provided.

The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and $L_3$ phases are thermodynamically stable systems. That is to say, they are not simply a meta-stable state that will separate and/or reform into layers, lamellar phases or the like, but are the stable thermodynamic form of the lipid/solvent mixture.

While the effectiveness of known lipid depot formulations is high, there are certain aspects in which the performance of these is less than ideal. One respect in which depot formulations could often be improved is in injection volume. Since the administration is only occasional, the absolute amount of active agent that must be administered is comparatively high, but the controlled-release vehicle (e.g. polymer or lipid depot formulation) must also be contained within the injection volume. Lower injection volume provides faster and more comfortable administration and improves patient compliance. However, doses are typically limited by the level to which the active agent can be incorporated into the depot precursor mixture. It would therefore be a considerable advantage to provide a precursor formulation in which greater levels of opioid active such as buprenorphine can be contained while maintaining controlled-release properties.

As indicated above, a class of active agents having particular utility as depot or slow-release formulations are opioids. The term "Opioids" as used herein encompasses a class of naturally occurring, semi-synthetic, and fully synthetic compounds which show agonistic and/or antagonistic properties for at least one opioid receptor. Opioids are of very great medical value, being highly effective analgesics. They are typically used for pain relief after serious injuries and/or medical procedures and for this use it can be of value to provide sustained dosing with a level or gently tapering concentration of active agent to correspond with a healing and recovery profile over a number of days or weeks.

Unfortunately, tolerance to, and physiological dependence upon, opioids can develop, and can lead to behavioural addiction, especially where fast-acting opioids are used and/or the drugs are abused. Furthermore, abuse of opioids is common because of the euphoric effects which can be caused by their sudden administration. Withdrawal from opioids where dependence has developed can be unpleasant, especially from fast-acting opioids which are commonly abused, such as diacetylmorphine (heroin) or fentanyl. One approach for assisting recovering addicts is thus to transfer them from fast-acting opioids to slower-acting drugs which can be taken less frequently without causing the symptoms of withdrawal. Patients may then be provided with a maintenance level of the slower-acting opioid or gradually weaned from this by a gently decreasing dose regime.

Typical candidates for use as this slower-acting "opioid-replacement" drug are methadone and buprenorphine, and studies have shown that these can significantly reduce the chances of relapse in recovering addicts. One of the advantages of these opioids over the abused substances is that they generally do not require administration so frequently in order to avoid withdrawal symptoms. Methadone, for example, needs to be administered daily, while the 37-hour half-life of buprenorphine means that a single dose is effective for 1-2 days, or longer in some patients. Weekly patches of buprenorphine are also available, although at present these are for use in pain management rather than in curbing addiction and have limited bioavailability. Excess drug is therefore used and waste patches are liable for misuse and misdirection.

The two primary dosing methods for these slow-acting opioids in addiction therapy are "detox", in which a tapering dose is provided over a period of around 2 weeks, and "maintenance", in which a level dose is provided over a longer term of, typically, a few months. In both cases, and with any of the known opioid preparations, frequent administration is generally required, which in turn requires on-going patient compliance. Evidently, it would be a considerable advantage to provide slow-release formulations which could be administered infrequently, and would provide a level, or gradually tapering, drug profile, to allow gradual detox or longer term maintenance without requiring frequent administration.

Previous lipid depot formulations of buprenorphine (e.g. U.S. Pat. No. 8,236,755) are highly effective, but provide a maximum of only around 9% buprenorphine concentration by weight. Polymeric systems, such as WO2001/154724, have been formulated with up to 20% buprenorphine but there remains scope for precursor formulations with enhanced drag loading levels.

The present inventors have now established that by appropriate choice of components, a pre-formulation comprising certain opioid active agents, particularly buprenorphine, can be formulated with a greater concentration of active agent than demonstrated hitherto while maintaining the controlled-release effect of the preparation. Certain of these precursor formulations (pre-formulations) are easy to manufacture, may be sterile-filtered, have low viscosity (allowing easy and less painful administration), allow a high bioavailability of active agent (thus allowing a smaller total amount of opioid to be used) and/or provide for effective dose control by means of control of active agent concentration and/or injection volume.

In a first aspect, the present invention thus a depot precursor formulation comprising:
  a) a controlled-release matrix;
  b) at least oxygen containing organic solvent;
  c) at least 12% by weigh of at least one active agent selected from buprenorphine and salts thereof, calculated as buprenorphine free base.

Such a depot precursor will typically form a depot composition in situ upon administration to the body of a subject. In the case of formulations comprising a lipid controlled-release matrix, this will typically be by uptake of aqueous fluid to form a structured (e.g. liquid crystal) phase. In the case of a polymer-based controlled-release matrix component the depot will generally be formed by loss of solvent.

Suitable controlled-release matrices thus include lipid controlled release formulations (as described herein) and polymeric release matrix systems (as described herein).

The high-loading depot precursor formulations of the present invention (as well as the other corresponding aspects) will typically comprise greater than 15% (e.g. 15 to 50%) by weight of active agent, preferably at least 21% and more preferably at least 25% by weight. Greater than 30% by weight is particularly preferred. Active agents will generally be buprenorphine or salts thereof as indicated herein.

In a second aspect, the present invention also provides a depot composition formed or formable from any of the depot precursor formulations described herein. Such a depot composition may comprise:
 a) a controlled-release matrix;
 b) optionally at least one oxygen containing organic solvent;
 c) at least 12% of at least one active agent selected from buprenorphine and salts thereof
 d) optionally at least one aqueous fluid.

Such a depot composition will typically be formed upon exposure of a precursor formulation of the present invention (such as any precursor formulation in any embodiment or preferred embodiment described herein) to an aqueous fluid in vivo. Exposure to such an aqueous fluid will generally result in a loss of solvent and/or an addition of water to the precursor formulation and may result in a phase change such as from solution to solid (a precipitation) or from a low-viscosity phase, such as a solution or $L_2$ phase to a high viscosity phase such as a liquid crystalline phase.

In a further aspect of the invention, there is also provided a method of sustained delivery of buprenorphine to a human or non-human animal body, said method comprising administering a depot precursor formulation comprising:
 a) a controlled-release matrix;
 b) at least oxygen containing organic solvent;
 c) at least 12% of at least one active agent selected from buprenorphine and salts thereof.

Preferably, the precursor formulation (pre-formulation) administered in such a method is a pre-formulation of the invention as described herein.

The method of administration suitable for the above method of the invention will be a method appropriate for the condition to be treated or addressed. A parenteral depot will thus be formed by parenteral (e.g. subcutaneous or intramuscular) administration. A bioadhesive non-parenteral (e.g. topical) depot composition may be formed by administration to the surface of skin, mucous membranes and/or nails, to ophthalmological, nasal, oral or internal surfaces or to cavities such as nasal, rectal, vaginal or buccal cavities, the periodontal pocket or cavities formed following extraction of a natural or implanted structure or prior to insertion of an implant (e.g a joint, stent, cosmetic implant, tooth, tooth filling or other implant).

Since the key medicinal properties of opioids are analgesia and use in detoxification and/or maintenance from opioid dependence, the formulations will typically be for systemic absorption, although topical pain relief can be provided by opioids and they are additionally of value in cough suppression (especially codeine and hydrocodone), diarrhoea suppression, anxiety due to shortness of breath (especially oxymorphone) and antidepression (especially buprenorphine). For these, appropriate administration methods, such as bioadhesive pain-relieving gels for topical pain, or non-absorbed oral compositions for diarrhoea suppression may be used.

In a further aspect, the present invention also provides a method for the formation of a depot composition comprising exposing a precursor formulation comprising:
 a) a controlled-release matrix;
 b) at least oxygen containing organic solvent;
 c) at least 12% by weight of at least one active agent selected from buprenorphine and salts thereof.
 to an aqueous fluid in vivo.

Suitable aqueous fluids are particularly body fluids as indicated herein. Preferably the pre-formulation administered is a pre-formulation of the present invention as described herein and more preferably a preferred formulation according to the present invention. The exposure to a fluid "in vivo" may evidently be internally within the body or a body cavity, or may be at a body surface such as a skin surface, depending upon the nature of the composition.

In a still further aspect the present invention provides a process for the formation of a precursor formulation suitable for the administration of an opioid bioactive agent to a (preferably mammalian) subject, said process comprising forming a mixture of
 a) a controlled-release matrix; and
 b) at least one oxygen containing organic solvent; and dissolving or dispersing at least 12% by weight of at least one buprenorphine in the mixture, or in at least one of components a, or b prior to forming the low viscosity mixture. Preferably the pre-formulation so-formed is a formulation of the invention as described herein. The process may additionally comprise sterilisation, such as by sterile filtration.

In a still further aspect, the present invention additionally provides for a method of treatment or prophylaxis of a human or non-human animal subject comprising administration of a precursor formulation as described herein. Such a method may be for the treatment of pain or for the treatment of drug dependence (typically opioid dependence) by detoxification and/or maintenance as described herein.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a 23 gauge (22 AWG/0.635 mm diameter) needle by manual pressure. In a further preferred embodiment, the low viscosity mixture should be a mixture capable of passing through a standard sterile filtration membrane such as a 0.22 μm syringe filter. In other preferred embodiments, a similar functional definition of a suitable viscosity can be defined as the viscosity of a pre-formulation that can be sprayed using a compression pump or pressurized spray device using conventional spray equipment. A typical range of suitable viscosities would be, for example, 0.1 to 5000 mPas, preferably 1 to 1000 mPas at 20° C. (e.g. 10 to 1000 mPas or 50 to 1000 mPas at 20° C.).

It has been observed that by the addition of small amounts of low viscosity solvent, as indicated herein, a very significant change in viscosity can be provided, particularly for lipid formulations (as described herein). As indicated in Example 11 below, for example, the addition of only 5% solvent (in the case of Example 11, ethanol) can reduce viscosity of a lipid mixture by several orders of magnitude. Addition of 10% solvent will cause a still greater effect. In order to achieve this non-linear, synergistic effect, in lowering viscosity it is important that a solvent of appropriately low viscosity and suitable polarity be employed. Such solvents include those described herein infra.

Particularly preferred examples of low viscosity mixtures are molecular solutions (of both polymer depot precursor formulations and lipid precursor formulations), suspensions of microbeads (of polymer matrices) and/or isotropic phases such as $L_2$ and/or $L_3$ phases (of lipid precursor formulations). As describe above, the $L_3$ is a non-lamellar phase of interconnected sheets which has some phase structure but lacks the long-range order of a liquid crystalline phase. Unlike liquid crystalline phases, which are generally highly viscous, $L_3$ phases are of lower viscosity. Obviously, mixtures of $L_3$ phase and molecular solution and/or particles of $L_3$ phase suspended in a bulk molecular solution of one or more components are also suitable. The $L_2$ phase is the so-called "reversed micellar" phase or microemulsion. Most preferred low viscosity mixtures are molecular solutions, $L_3$ phases and mixtures thereof. $L_2$ phases are less preferred, except in the case of swollen $L_2$ phases as described herein.

The present invention provides a pre-formulation comprising components a, b and at least 12% of at least one opioid bioactive agent as indicated herein. In one particularly preferred embodiment, the controlled release matrix component a) comprises a lipid controlled release formulation. Such a formulation will preferably comprise:

i) at least one neutral diacyl and/or triacyl lipid and/or a tocopherol; and
ii) at least one phospholipid;

A preferably embodiment of this will be:
i) at least one neutral diacyl lipid and/or a tocopherol; and
ii) at least one phospholipid;

One of the considerable advantages of the lipid precursor formulations of the invention is that components i) and ii) may be formulated in a wide range of proportions. In particular, it is possible to prepare and use pre-formulations of the present invention having a much greater proportion of phospholipid to neutral, diacyl lipid and/or tocopherol than was previously achievable without risking phase separation and/or unacceptably high viscosities in the pre-formulation. The weight ratios of components i):ii) may thus be anything from 5:95 right up to 95:5. Preferred ratios would generally be from 90:10 to 20:80 and more preferably from 85:15 to 30:70. A highly suitable range is i):ii) in the ratio 40:60 to 80:20, especially around 50:50, e.g. 45:55 to 60:40. In one preferred embodiment of the invention, there is a greater proportion of component ii) than component i). That is, the weight ratio i):ii) is below 50:50, e.g. 48:52 to 2:98, preferably, 40:60 to 10:90 and more preferably 35:65 to 20:80. In an alternative and highly valuable embodiment, there may be an equal or greater amount of component i) in comparison with component ii). In such an embodiment, there may be, for example, a weight ratio of 50:50 to 80:20 of components i) to ii). A ratio of 50:50 to 70:30 may also be suitable.

Corresponding to the above, the amount of component i) in the precursor formulations may be, for example, 10% to 90% (e.g. 18 to 90%) by weight of the total formulation, preferably 10% to 70%, such as 12% to 40% or 12% to 30% by weight of the total formulation. In one embodiment, the absolute amount of component i) by weight is no less than the amount of component ii).

Similarly, the amount of component ii) in the precursor formulations may be, for example, 8% to 90% (e.g. 18 to 90%) by weight of the total formulation, preferably 8% to 70%, such as 10% to 40% or 10% to 30% by weight of the total formulation.

The total amount of component a) in the formulation will typically be 20 to 70%, such as 30 to 60 wt % based upon the weight of the total formulation.

In an alternative embodiment of the invention, component a) may comprise at least one polymer release matrix. Such matrices are typically biodegradable polymers.

Such polymers are well known in the art and may be homopolymers, mixtures of homopolymers, copolymers, mixtures of copolymers and/or mixtures of homopolymers and copolymers. Polyesters and/or polyamides are particularly suitable, of which biodegradable polyesters are preferred. Examples of suitable polyesters include polylactate, polyglycolate, polylactate-co-glycolate (polylactate/glycolate copolymer) and mixtures thereof. Polylactate-co-glycolate (PLGA) is particularly suitable.

Polymers may be in the form of a solution or may be used as microspheres (microbeads) in suspension. PLGA microspheres are one preferred embodiment.

The amount of component b in the pre-formulations of the invention will be at least sufficient to provide a low viscosity mixture (e.g. a molecular solution, see above) of components a, b and the buprenorphine active, and will be easily determined for any particular combination of components by standard methods. The phase behaviour of lipid formulations may be analysed by techniques such as visual observation in combination with polarized light microscopy, nuclear magnetic resonance, x-ray or neutron diffraction, and cryo-transmission electron microscopy (cryo-TEM) to look for solutions, $L_2$ or $L_3$ phases, or liquid crystalline phases. Viscosity may be measured directly by standard means. As described above, an appropriate practical viscosity is that which can effectively be syringed and particularly sterile filtered. This will be assessed easily as indicated herein.

A key feature of the present invention is the facility to incorporate a higher level of buprenorphine active agent (e.g, buprenorphine or a salt thereof) than has been observed previously. The present inventors have observed that the capability of a low-viscosity mixture to contain buprenorphine active agent is greatly enhanced by the inclusion of at least one amide solvent in component b). Correspondingly, component b) preferably comprises at least one amide. As a comparison, for example, a lipid formulation prepared with ethanol as component b) can typically dissolve up to 9% of buprenorphine active agent. When an amide solvent such as NMP is utilised, this can increase to 35% or greater while maintaining a valuable release profile. Particularly preferred amide compounds which may be comprised in component b) include N-Methyl-2-pyrrolidone (NMP) dimethyl formamide (DMF) and dimethyl acetamide (DMA). NMP is most preferred.

The weight of solvent component b incorporated into the precursor formulation will depend crucially upon the type of sustained release formulation a) that is in use. For example, a polymeric sustained release formulation in solution might require the solvent to be present at 40 to 70% by weight in order to ensure a sufficiently low viscosity and full solubilisation. In contrast, the solvent level typically used for a lipid-based controlled release formulation would generally be around 0.5 to 50% of the total weight of the precursor formulation. For the high loading compositions of the present invention, this proportion is preferably (especially for injectable depots) 20 to 40% and more preferably 20 to 38% or 25 to 35% by weight. A highly suitable range is around 30%, e.g. 15 to 45%, especially, 10 to 30% or 10 to 40% by weight of the complete composition. Thus, overall, a solvent level of 1 to 50% of the total precursor formulation weight is appropriate and suitable ranges for each embodiment will be clear to those with experience in the art. In one embodiment, a precursor formulation and corresponding depot & method are provided in which the administration period is one dose each month and the solvent content is 30%±10%.

Component "i)" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Preferred polar head groups are non-ionic and include polyols such as glycerol, diglycerol and sugar moieties (such as inositol and glucosyl based moieties); and esters of polyols, such as acetate or succinate esters. Preferred polar groups are glycerol and diglycerol, especially glycerol.

Diacyl glycerols of component i) will comprise glycerol and two acyl chains as indicated herein. Correspondingly, triacyl glycerols are preferred triacyl lipids and they will comprise a glycerol "head" group and three independently chosen acyl chains as indicated herein. Preferred aspects as indicated herein will apply correspondingly.

In one preferred aspect, component i) is a diacyl lipid in that it has two non-polar "tail" groups. This is generally preferable to the use of mono-acyl ("lyso") lipids because these are typically less well tolerated in vivo. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid. In one preferred embodiment, component i) comprises components with C16 to C18 alkyl groups, particularly such groups having zero, one or two unsaturations. In particular, component i) may comprise at least 50% of components having such alkyl groups.

The diacyl lipid, when used as all or part of component "i)", may be synthetic or may be derived from a purified and/or chemically modified natural sources such as vegetable oils. Mixtures of any number of diacyl lipids may be used as component i). Most preferably this component will include at least a portion of diacyl glycerol (DAG), especially glycerol dioleate (GDO). In one favoured embodiment, component i) consists of DAGs. These may be a single DAG or a mixture of DAGs. A highly preferred example is DAG comprising at least 50%, preferably at least 80% and even comprising substantially 100% GDO.

An alternative or additional highly preferred class of compounds for use as all or part of component i) are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

Tocopherol

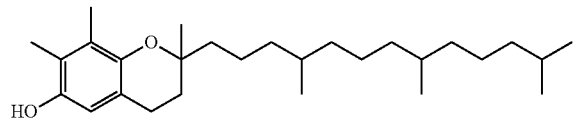

In one embodiment of the invention, component i) consists essentially of tocopherols, in particular tocopherol as shown above.

A preferred combination of constituents for component i) is a mixture of at least one DAG (e.g. at least one C16 to C18 DAG, such as GDO) with at least one tocopherol. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component "ii)" in lipid embodiments of the present invention is at least one phospholipid. As with component i), this component comprises a polar head group and at least one non-polar tail group. The difference between components i) and ii) lies principally in the polar group. The non-polar portions may thus suitably be derived from the fatty acids or corresponding alcohols considered above for component i). In particular C16 to C18 acyl groups having zero, one or two unsaturations are highly suitable as moieties forming the non-polar group of the compounds of component ii). It will typically be the case that the phospholipid will contain two non-polar groups, although one or more constituents of this component may have one non-polar moiety. Where more than one non-polar group is present these may be the same or different.

Preferred phospholipid polar "head" groups include phosphatidylcholine (PC), phosphatidylethanolamine (PE), phosphatidylserine (PS) and phosphatidylinositol (PI). PC and PE are preferred lipids, both individually and as a mixture. In one embodiment, component b) may comprise at least 70% PC, PE or mixtures thereof. Most preferred is phosphatidylcholine (PC). In a preferred embodiment, component ii) thus comprises at least 50% PC, preferably at least 70% PC and most preferably at least 80% PC. Component ii) may consist essentially of PC.

The phospholipid portion, even more suitably than any diacyl lipid portion, may be derived from a natural source. Suitable sources of phospholipids include egg, heart (e.g. bovine), brain, liver (e.g. bovine) and plant sources including soybean. Such sources may provide one or more constituents of component ii), which may comprise any mixture of phospholipids.

Since the pre-formulations of the invention are to be administered to a subject for the controlled release of an active agent, it is preferable that the components i) and ii), as well as any alternative controlled release matrix are biocompatible. In this regard, it is preferable to use, for example, diacyl lipids and phospholipids rather than monoacyl (lyso) compounds. A notable exception to this is tocopherol, as described above. Although having only one alkyl chain, this is not a "lyso" lipid in the convention sense. The nature of tocopherol as a well tolerated essential vitamin evidently makes it highly suitable in biocompatibility.

It is furthermore most preferable that the lipids and phospholipids of components i) and ii) are naturally occurring (whether they are derived from a natural source or are of synthetic origin). Naturally occurring lipids tend to cause lesser amounts of inflammation and reaction from the body of the subject. Not only is this more comfortable for the subject but it may increase the residence time of the resulting depot composition, especially for parenteral depots, since less immune system activity is recruited to the administration site. In certain cases it may, however, be desirable to include a portion of a non-naturally-occurring lipid in components i) and/or ii). This might be, for example an "ether lipid" in which the head and tail groups are joined by an ether bond rather than an ester. Such non-naturally-occurring lipids may be used, for example, to alter the rate of degradation of the resulting depot-composition by having a greater or lesser solubility or vulnerability to breakdown mechanisms present at the site of active agent release. Although all proportions fall within the scope of the present invention, generally, at least 50% of each of components i) and ii) will be naturally occurring lipids. This will preferably be at least 75% and may be up to substantially 100%.

Two particularly preferred combinations of components i) and ii) are GDO with PC and tocopherol with PC, especially in the region 10-30 wt % GDO/tocopherol, 5-25 wt % PC and 20-40% solvent (especially comprising NMP). A composition of 15-25% GDO, 10-25% PC, with 20-35%, preferably 25-32% solvent (e.g. NMP and optionally at least one of ethanol, benzyl alcohol, propylene glycol, benzyl benzoate, dimethylsulphoxide etc) and 12-45% (e.g. 31 to 40%), preferably 15-40% of at least one opioid active agent is particularly effective. A ratio of PC/GDO: ~0.25-1.5, preferably 0.6-1.2 is desirable in many cases (including other embodiments indicated herein).

In addition to amphiphilic components i) and ii), lipid-based pre-formulations of the invention may also contain additional amphiphilic components at relatively low levels. In one embodiment of the invention, the pre-formulation contains up to 10% (by weight of components i) and ii)) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable fatty acids are palmitic, stearic, oleic and linoleic acids, particularly oleic acid. The formulations of the invention comprising diacyl lipids may also contain up to 10% of an optional triacyl glycerol, such as those described herein.

Component "b" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Typical solvents suitable for use as component b) include at least one solvent selected from alcohols, ketones, esters (including lactones), ethers, amides (including lactams) and sulphoxides. Examples of suitable alcohols include ethanol, isopropanol, benzylalcohol and glycerol formal. Monools are preferred to diols and polyols. Where diols or polyols are used, this is preferably in combination with an at least equal amount of monool or other preferred solvent. Examples of ketones include acetone and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides and sulphoxides include dimethylacetamide (DMA), n-methyl pyrrolidone (NMP), 2-pyrrolidone and dimethylsulphoxide (DMSO). Less preferred solvents include dimethyl isosorbide, tetrahydrofurfuryl alcohol, diglyme and ethyl lactate. The high loading nature of the precursor formulations is believed to be enabled or enhanced by the presence of at least one amide solvent. NMP is a highly preferred solvent for use in combination with buprenorphine. In one embodiment, component b) therefore comprises NMP and may comprise at least 50% or at least 70% NMP. Component b) may consist essentially of (e.g. >95%) or consist of NMP. NMP and ethanol is a further preferred combination and component b) may comprise or consist of a mixture of NMP and ethanol.

Since the pre-formulations are to be administered to a living subject, it is necessary that the solvent component b) is sufficiently biocompatible. The degree of this biocompatibility will depend upon the application method and the volume injected. Furthermore, since component b) may be any mixture of solvents, a certain amount of a solvent that would not be acceptable in large quantities may evidently be present. Overall, however, the solvent or mixture forming component b) must not provoke unacceptable reactions from the subject upon administration. Generally such solvents will be hydrocarbons or preferably oxygen containing hydrocarbons, both optionally with other substituents such as nitrogen containing groups. It is preferable that little or none of component b) contains halogen substituted hydrocarbons since these tend to have lower biocompatibility. Where a portion of halogenated solvent such as dichloromethane or chloroform is necessary, this proportion will generally be minimised. Where the depot composition is to be formed non-parenterally a greater range of solvents may evidently be used than where the depot is to be parenteral.

Component b) as used herein may be a single solvent or a mixture of suitable solvents but will generally be of low viscosity. This is important because one of the key aspects of the present invention is that it provides preformulations that are of low viscosity and one primary role of a suitable solvent is to reduce this viscosity. This reduction will be a combination of the effect of the lower viscosity of the solvent and the effect of the molecular interactions between solvent and controlled release formulation, such as the polymer or lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component b) (single solvent or mixture) should typically be no more than 18 mPas at 20° C. This is preferably no more than 15 mPas, more preferably no more than 10 mPas and most preferably no more than 7 mPas at 20° C.

The solvent component b) will generally be at least partially lost upon in vivo formation of the depot composition, or diluted by absorption of water from the surrounding air and/or tissue. It is preferable, therefore, that component b) be at least to some extent water miscible and/or dispersible and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example to decrease the rate of evaporation of the solvent from the pre-formulation in order to control the rate of liquid crystalline depot formation.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less than 0.5% by the weight of the pre-formulation. In one preferred aspect, the pre-formulations of the invention do not contain glycerol, ethylene glycol or propylene glycol and contain no more than a trace of water, as just described.

There is, however, a certain embodiment of the present invention in which higher proportions of water may be tolerated. This is where water is present as a part of the solvent component in combination with an additional water-miscible component b (single solvent or mixture). In this embodiment, up to 15 wt % water may be present providing that at least 3 wt %, preferably at least 5% and more preferably at least 7 wt % component b is also present, that component b is water miscible, and that the resulting pre-formulation remains non-viscous and thus does not form a liquid crystalline phase. Generally there will be a greater amount of component b) by weight than the weight of water included in the preformulation. Most suitable solvents of use with water in this aspect of the invention include ethanol, isopropyl alcohol and NMP.

A key aspect of the present invention is that high loadings of BUP may be used to reduce the injection volume necessary for a particular dose of buprenorphine (BUP). In one embodiment, the compositions of the present invention thus contain at least 140 mg/mL (e.g. 140 to 500 mg/mL) of buprenorphine, preferably at least 200 mg/mL and more preferably at least 300 mg/mL. A loading level of at least 340 mg/mL is possible and advantageous in reducing injection volumes.

The pre-formulations of the present invention contain one or more buprenorphine bioactive agents (described equivalently as "bioactive agents", "opioid active agents" or simply "active agents" herein). Active agents may be any suitably biotolerable form of any buprenorphine compound having an effect (e.g. agonism and/or antagonism) at one or more opioid receptors. Buprenorphine free base is the most preferred buprenorphine active agent and where weight percentages are specified herein, these are in terms of the equivalent amount of buprenorphine free base unless otherwise specified. Suitable salts, including mixtures thereof, may be used and these salts may be any biocompatible salt. Suitable salts include acetate, citrate, pamoate or halide (e.g. chloride or bromide) salts, or any of the many biocompatible salts which are known in the art.

Buprenorphine is an opioid with mixed agonist-antagonist properties (also known as a partial agonist) that has been used in the treatment of opioid dependence in a number of countries. It is approved by the Food and Drug Administration (FDA) for the treatment of opioid dependence in the United States and clinical studies have shown buprenorphine to be effective in reducing opioid-positive urines and retaining patients in outpatient maintenance treatment of opioid dependence, as well as in the detoxification of opioid abusers.

Buprenorphine has a unique pharmacological profile with several potential strengths over other opioid treatments:

1. A ceiling on its agonist activity that may reduce its abuse liability and contribute to a superior safety profile.

2. Attenuation of physiological and subjective effects which likely contributes to the suppression of opioid self-administration.

3. Slow receptor dissociation providing extended duration.

Importantly, buprenorphine treatment is associated with a relatively low-intensity withdrawal syndrome upon discontinuation, making it particularly promising for detoxification treatments.

Buprenorphine is currently available in sublingual dosing forms, which require dosing every 1-2 days either at a clinic, or with "take-home" medication. Because of the potential for abuse of opioids, however, "take-home" of any opioid poses potential logistic and legislative problems. This is made more problematic by the low bioavailability of existing sublingual formulations meaning that the dose being "taken home" is potentially quite a significant one.

A depot formulation of the present invention offers several advantages in use for treating opioid dependence, including fast onset and relatively stable levels of buprenorphine over time, thereby suppressing withdrawal symptoms and blocking the effects of exogenously-administered opioids for several weeks. The slow decay and elimination of the depot buprenorphine could also provide a gradual opioid detoxification with minimal withdrawal syndrome. Hence, a buprenorphine depot may offer a promising approach for delivering effective opioid maintenance or detoxification treatment. Furthermore, a depot formulation should minimize the burdens of patient compliance as it would require a less frequent dosing regimen, thereby also reducing the frequency of clinic visits and the amount of clinical support needed. Finally, depot buprenorphine should reduce the risks of misuse and drug diversion of the medication by eliminating or reducing the need for take-home medication.

In one embodiment of the present invention, the bioavailability of buprenorphine as measured from time zero to time of last measurement and extrapolated to infinity for a single dose, or between two consecutive doses at steady state, as the area under the curve of human plasma concentration against time is no less than 3 hours*ng/mL per mg, preferably no less than 5 hours*ng/ml per mg of administered buprenorphine, preferably no less than 7 and more preferably no less than 10 h ng/ml per mg of administered buprenorphine. This compares with less than 3 hour ng/ml per mg administered by current sublingual formulations.

Current sublingual formulations include Subutex® and Suboxone®. Both are sublingual tablets approved by the FDA for the treatment of opioid addiction. Subutex contains only buprenorphine hydrochloride as active agent. This formulation was developed as the initial product. The second medication, Suboxone also contains naloxone to guard against misuse. Subutex is typically given during the first few days of treatment, while Suboxone is used during the maintenance phase of treatment. Both of these products contain a relatively large dose of buprenorphine because of their relatively low bioavailability. Thus, there is a risk of diversion of these products, especially since they are often prescribed for self-administration. These FDA approved products are: Subutex (bitter sublingual, no active additives; in 2 mg and 8 mg dosages) and Suboxone (Lemon-lime flavored sublingual, one part naloxone for every four parts buprenorphine; hexagon shaped tablet in 2 mg and 8 mg dosages). The existing Suboxone product is also available in a clinically interchangeable "sublingual film" formulation. This film product remains a once-daily dosage product and although it produces a somewhat higher Cmax than the sublingual tablet, the plasma profile and bioavailability are very similar to the tablet. The film product is thus available in the same 8 mg and 2 mg dosages as the sublingual tablet product.

The precursor formulations and all corresponding aspects of the present invention may be formulated with buprenorphine as the sole active agent. However, in one embodiment, the various formulations of the invention may be prepared as combination medicaments (e.g. with other opioid agonists and/or antagonists). For example, naloxone may be formulated with buprenorphine (e.g. at between 1:1 and 10:1 buprenorphine:naloxone by wt). Other opioids may similarly be formulated with the buprenorphine active agent of the present invention. This will apply particularly to precursor formulations intended for pain control such as by analgesia.

A further key aspect of the present invention is the comparatively low Cmax (peak plasma concentration) in comparison with the dose administered and the period over which the drug is effective. Administration of 16 mg of buprenorphine as Subutex gives a Cmax concentration of 6 ng/mL but is cleared to around 0.5 ng/mL in less than 24 hours. In comparison, a 15 mg dose administered as a formulation of the present invention peaks with a Cmax of around 3.5 and remains at around 0.9 ng·mL at 7-days following administration.

Thus in a further preferred aspect, the compositions of the present invention provide a Cmax (maximum concentration) in human blood plasma after a single administration of no more than 0.3 ng/ml per mg of administered buprenorphine. This will preferably be no more than 0.22 ng/mL per mg of buprenorphine administered and more preferably no more than 0.17 ng/mL per mg administered. It can be seen in comparison that Subutex gives a peak concentration of at least around 0.4 ng/mL per mg of buprenorphine administered.

A still further advantage of the compositions of the present invention is the linearity of the AUC dose experienced by the subject in comparison with the administered dose of buprenorphine. This may be seen from FIG. 6 and allows the physician to control the experienced dose directly by control of the administered dose in a linear relationship. It can furthermore be seen that Cmax is additionally observed to vary linearly with administered dose and again this allows the medical professional to control of the concentration experienced by the subject (FIG. 5). This linear or substantially linear relationship of AUC to injected dose is also termed "dose proportionality".

The compositions of the invention provide for an extended duration of buprenorphine release, e.g., as exemplified in FIG. 4. Thus, the half-life plasma concentration experienced by the subject after Cmax may be greater than 1 day, preferably greater than 2 days and most preferably greater than 3 days.

Because of the relatively low Cmax and the long half-life of the buprenorphine depot-precursor formulations of the present invention, the variation of plasma concentration during a cycle of administration (once a steady-state has been achieved) will be less pronounced (and obviously less sudden) than is experienced by a subject taking a daily administration product. For example, the steady-state variation between Cmax (the highest plasma concentration during a cycle of administration) and Cmin (the lowest plasma concentration over an administration cycle at steady-state (also termed Ctrough)) may be no more than 20-fold. Thus the steady-state Cmax concentration may be no more than 20 times the Cmin plasma concentration, preferably no more than 15 times and more preferably no more than 10 times. Most preferably the Cmax/Cmin ratio will be no more than 6.

Thus, the variation between Cmin and Cmax at a steady-state of administration of the products of the present invention may fall with the range of between 0.4 ng/mL and 10 ng/mL, preferably falling within the range of 0.5 ng/mL and to 8 ng/mL. Such a range is highly suitable for treatment of opioid dependence or for opioid maintenance therapy.

Because of the very high bioavailability of the buprenorphine formulated in the preformulations of the present invention, the transition of a subject currently receiving daily sublingual buprenorphine to receiving, for example, monthly or weekly formulations according to the present invention will not generally require that the dose be increased significantly. For example a subject may transfer from daily sublingual buprenorphine to a weekly formulation of the present invention and receive 0.5 to 3 times his previous daily dose administered weekly. Preferably the weekly dose will be 0.5 to 2 times the previous daily maintenance dose.

The amount of bioactive agent to be formulated with the pre-formulations of the present invention will depend upon the functional dose and the period during which the depot composition formed upon administration is to provide sustained release. Typically, the dose formulated for a particular agent will be less than half of the equivalent of the normal daily dose multiplied by the number of days the formulation is to provide release. Preferably this will be less than one third and more preferably less than one quarter of the total of the daily doses administered to that subject. Thus, for example, a subject receiving a daily sublingual dose of 8 mg buprenorphine might typically receive around 22.5 mg every seven days as formulated according to the present invention.

The present inventors have observed that the blood plasma buprenorphine concentration at which a subject requires a "rescue" dose of buprenorphine correlates directly to the maintenance dose that the subject was receiving prior to transfer to a depot composition. This is shown graphically in FIG. 10. It can be seen from that figure that the "minimum effective" plasma level for opioid maintenance therapy varied from around 0.2 ng/mL to around 1 ng/mL as the previous mean maintenance dose for the different dose groups varied from 7 to 17 mg/day. Correspondingly, a lower dose of around 20-30 mg/month buprenorphine formulated according to the present invention might be appropriate for those on a daily dose of up to 7 mg/day, while 50 to 100 mg/month might be appropriate for those transitioning from a daily dose of up to 17 mg/day.

Since different subjects will have differing tolerance for opioids, it is important that a suitable dose can be selected by a medical professional which will provide peak and plateau concentrations which are acceptable to that subject.

Doses suitable for a once-weekly administration would typically be in the range 3 to 40 mg buprenorphine (calculated as buprenorphine free base), preferably 5 to 30 mg per week.

Doses suitable for a once-fortnightly administration would typically be in the range 6 to 60 mg buprenorphine (calculated as free base), preferably 10 to 50 mg per two weeks (i.e. per administration).

Doses suitable for once-monthly administration would typically be in the range 10 to 200 mg buprenorphine (calculated as free base), preferably 10 to 180 mg per month (i.e. per administration). For a opioid substitution (maintenance) dose, 40-140 mg per month would be preferred. For a pain relieving dose, 10 to 50 mg per month would be appropriate.

For opioid dependence and poioid maintenance therapy, a dose providing a blood plasma concentration of at least 0.2 ng/mL (e.g. at least 0.4 or at least 0.8 or at least 1.0 ng/mL) is preferred.

Evidently this amount will need to be tailored to take into account factors such as body weight, gender, and in particular opioid tolerance and current treatment regime. The precise amount suitable in any case will readily be determined by one of skill in the art.

In a further advantage of the present invention, the formulations described herein provide a very stable equilibrium level of buprenorphine once a small number of cycles of regular administration have been made. This stable level provides for excellent maintenance dosing and avoidance of withdrawal symptoms. Furthermore, once a subject is stabilised by, for example, receipt of weekly buprenorphine depot injections, that subject may then be moved onto bi-weekly (fortnightly) formulations and in due course monthly formulations.

Furthermore, because the blood concentration of buprenorphine decays with a half-life of 3-4 days, no sudden drop in plasma concentration is experienced and this may help avoid or lessen withdrawal symptoms if the subject elects to come off from opioid maintenance. Thus a treatment regime may involve the transfer from daily to weekly to fortnightly to monthly formulations. A transition may then be made to lower doses and in due course the very slow decay from a stable plateau may allow withdrawal of opioid treatment with minimal withdrawal symptoms.

One key advantage of the various formulations of the present invention is that they permit the inclusion of buprenorphine at surprisingly high loadings. This allows for decreased injection volumes, less pain on injection and at the injection site and thus better patient compliance. Thus, the overall total buprenorphine content in the precursor formulations of the present invention will typically be 12% to 55% by weight of the total formulation. This may be chosen to be in a suitable range for any particular application and may thus be, for example in the ranges 15 to 25% or 30 to 50%. In one particularly preferred embodiment, higher buprenorphine loadings are used in combination with the use of NMP as at least a part (e.g. at least 50% of component b)) of the solvent component. Thus, precursor formulations comprising NMP may have a buprenorphine loading of greater than 30%, for example 31% to 55%, 32% to 55% or 35% to 50%.

In one embodiment, precursor formulations and all corresponding aspects of the present invention include a polymer release matrix (as described herein) and comprise buprenorphine at greater than 30% by weight (e.g. 31 to 50% by weight). Such compositions will typically comprise NMP.

In an alternative embodiment, the precursor formulations and all corresponding aspects of the present invention include a lipid release matrix (as described herein) and comprise buprenorphine at greater than 12% by weight (e.g. 12 to 50% by weight, preferably 25 to 50%, e.g. 31 to 50% by weight). Such compositions will typically comprise NMP.

In a key embodiment, the pre-formulations of the present invention will generally be administered parenterally. This administration will generally not be an intra-vascular method but will preferably be subcutaneous, intracavitary or intramuscular. Typically the administration will be by injection, which term is used herein to indicate any method in which the formulation is passed through the skin, such as by needle, catheter or needle-free injector.

Injection volumes for the precursor formulations of the present invention may be reduced because of the uniquely high level of active agent incorporated. Injection volumes will preferably be no more than 5 ml per administration, more preferably no more than 2 ml and most preferably no more than 1 ml. The prefilled devices of the invention will thus typically contain these volumes of composition. Pre-filled devices such as syringes containing ready-to-use precursor formulations (especially comprising lipid matrices but also possible with the polymer formulations of the present invention) of the present invention thus form a further aspect thereof.

One highly valuable aspect of the present invention relates to the use of lipid controlled release matrices in the formation of the precursor formulations and depot compositions of the invention. Such lipid matrices are described herein and in documents cited herein.

The lipid-based pre-formulations of the present invention provide non-lamellar liquid crystalline depot compositions upon exposure to aqueous fluids, especially in vivo and in contact with body surfaces. As used herein, the term "non-lamellar" is used to indicate a normal or reversed liquid crystalline phase (such as a cubic or hexagonal phase) or the $L_3$ phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. By use of the lipid pre-formulations of the present invention it is possible to generate any phase structure present in the phase-diagram of components i) and ii) with water. This is because the pre-formulations can be generated with a wider range of relative component concentrations than previous lipid depot systems without risking phase separation or resulting in highly viscous solutions for injection. In particular, the present invention provides for the use of phospholipid concentrations above 50% relative to the total amphiphile content. This allows access to phases only seen at high phospholipid concentrations, particularly the hexagonal liquid crystalline phases.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives.

In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the preformulations of the present invention are of low viscosity. As a result, these preformulations must not be in any bulk liquid crystalline phase since all liquid crystalline phases have a viscosity significantly higher than could be administered by syringe or spray dispenser. The preformulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component b) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. This takes the form of generation of a non-lamellar phase from lipid-based controlled release matrices or precipitation of a polymeric monolith in the case of polymer solution precursor formulations. Generally, this will be a transition from a molecular (or polymer) solution, swollen $L_2$ and/or $L_3$ phase to one or more (high viscosity) liquid crystalline phases or solid polymer. Such phases include normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes or less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion and/or evaporation) and in some cases take in aqueous fluid from the bodily environment (e.g. moist air close to the body or the in vivo environment) such that at least a part of the lipid formulations generate a non-lamellar, particularly liquid crystalline phase structure. Polymeric precursor solutions lose solvent to the biological environment and precipitate a solid polymer. In most cases these non-lamellar structures are highly viscous and are not easily dissolved or dispersed into the in vivo environment and are bioadhesive and thus not easily rinsed or washed away. Furthermore, because the non-lamellar structure has large polar, apolar and boundary regions, it is highly effective in solubilising and stabilising many types of active agents and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water. In fact, very high performance is provided in comparison with existing formulations. In one embodiment, the invention thus provides injectable preformulations and resulting depot compositions wherein the highest plasma concentration of active after administration is no more than 5 times the average concentration between 24 hours and 5 days of administration. This ratio is preferably no more than 4 times and most preferably no more than 3 times the average concentration.

It is a considerable advantage of both the lipid-containing precursor formulations and the polymer-matrix precursor formulations of the present invention that they may be provided in storage-stable, ready-to-administer form. That is to say, the precursor formulations of the present invention may be provided in a form that requires no further combining of components in order to generate a formulation that is suitable for injection. Thus the invention correspondingly provides an administration device containing at least one precursor formulation as described herein wherein the formulation is ready for administration and/or administrable without any further combination or mixing of components. This contrasts with many controlled-release products, particularly polymeric controlled-release formulations, which require various components to be combined before delivery to the patient. Such an administration device will typically contain a dose suitable for a single administration where the administration may be once-weekly, once-fortnightly, once-monthly or once every two or three months. In all cases, the dose of buprenorphine will be selected so as to provide over the whole of the dosing period (at steady state) a Cmax and Cmin that are within the Cmax to Cmin range experienced following daily sublingual buprenorphine administration. Suitable administration devices include prefilled syringes with optional needle stick prevention safety device and/or auto-injector, pen cartridge systems and similar devices.

Suitable administration devices of the invention include a ready-to-use buprenorphine formulation of the present invention in a cartridge pen combination or prefilled syringe device, optionally equipped with a needle stick protecting safety device or auto-injector. The device may have a needle with a gauge higher than 18 G, preferably above 20 G, more preferably above 22 G (for example 23 G or 25 G). The buprenorphine formulation will generally be a precursor formulation as described herein in any embodiment. Such a formulation will generally have a viscosity in the range of 100-500 mPas.

For ease of self-administration, the device of the present invention may be or may be used with or incorporated into an auto-injection device or pen-cartridge device. Such a device may be disposable or reusable.

By "storage stable" as used herein is indicated that a composition maintains at least 90% of the original active agent content after storage for 36 months at 25° C. and 60% relative humidity. This is preferably at least 95% and more preferably at least 98%.

A ready-to-administer product has obvious advantages for ease of administration and in particular, if a opioid dependence product or long term pain relief medication is to be administered by a healthcare professional at regular intervals to a population of patients, a significant amount of time may be required in preparation of the materials prior to injection. In contrast, if the product is ready to use or even provided in a pre-filled administration device then the healthcare professional may spend their time in consultation with patients rather than in mixing medications.

The methods of treatment and/or prophylaxis, and corresponding uses in manufacture, of the present invention will be for any medical indication for which opioids are indicated. In particular, chronic conditions such as chronic pain (e.g. in arthritis, after surgery, in palliative cancer treatment etc.) are particularly suitable for the use of the present depot formulations and their precursors. The most suitable indications will, however, include pain, diarrhoea, depression, opioid dependence, opioid addiction, and the symptoms of opioid withdrawal. Of these, the present compositions are most preferably used in methods for the treatment and/or prophylaxis of opioid dependence, opioid addiction, and/or the symptoms of opioid withdrawal. Opioid maintenance therapy (opioid substitution therapy) is the most preferred treatment method for use of the formulations of the invention.

Cases where opioid dependence and/or opioid addiction have resulted from opioid abuse are particularly suitable for treatment with the present compositions because they offer advantages in terms of patient compliance, where the patient's lifestyle may not be compatible with regular attendance at a clinic or other site of medical treatment.

In one aspect, the present invention therefore provides for a method of detoxification treatment of a (preferably human) mammalian subject where the subject has or has had an opioid dependence, addiction, or habit, and/or where the subject is suffering from or is at risk of suffering from withdrawal symptoms from opioid administration. Such a detoxification method will comprise at least one administration of a precursor formulation of the present invention. Such a formulation may be any such formulation as described herein and as evident from that disclosure.

In a further aspect, the present invention therefore provides for a method of maintenance treatment of a (preferably human) mammalian subject where the subject has or has had an opioid dependence, addiction, or habit, and/or where the subject is suffering from or is at risk of suffering from withdrawal symptoms from opioid administration. Such a maintenance treatment method will comprise at least one and more commonly multiple administrations of a precursor formulation of the present invention. Such a formulation may be any such formulation as described herein and as evident from that disclosure. Such administrations may be, for example, once weekly, once every two weeks (fortnightly) or once monthly.

In a similar aspect, the present invention provides a method for opioid maintenance therapy comprising at least six administrations (e.g. 6-120 administrations) of precursor formulations of the present invention at periods of 28±7 days between each administration.

It is notable that the low ratio of Cmax to Cmin over 28 days provided by the products of the present invention demonstrate that a highly effective once-monthly formulation can be generated according to the present invention. It is preferable that the ratio of Cmax to Cmin over 28 days be no more than 200, preferably no more than 50, or no more than 10. preferably no more than 5, more preferably no more than 3 and most preferably no more than 2.8, measured as plasma buprenorphine concentrations.

In one key aspect, the precursor formulations of the invention are given as a subcutaneous injection. Compared with the sublingual buprenorphine products on the market, the products of the invention have one or more of the following advantages: 1) Rapid therapeutic onset (with maximum plasma concentrations established within 24 hours after injection) followed by steady long-acting release, 2) Reduced variation in buprenorphine plasma levels over time (stable plasma levels attained for at least 7 days) resulting in more therapeutic levels and a possible reduction in morning "cravings", 3) Less frequent dosing resulting in reduced frequency of clinic visits and need for medical support, 4) Significantly higher bioavailability and efficacy-over-dose ratio, meaning less drug substance in circulation and on the street, 5) Decreased risk of drug diversion, 6) Easier dose adjustment, 7) "Ready-to-use" dosage formulation, 8) high buprenorphine loading, 9) good systemic tolerability and 10) good local tolerability at the administration site.

The Invention will now be further illustrated by reference to the following non-limiting Examples and the attached Figures, in which;

FIG. 1 shows the cumulative release of methylene blue (MB) from a depot formulation comprising PC/GDO/EtOH (45/45/10 wt %) when injected into excess water;

FIG. 2 demonstrates the non-linear decrease of pre-formulation viscosity upon addition of N-methyl pyrolidone (NMP) and ethanol (EtOH); Specifically, FIG. 2 illustrates a decrease in viscosity at 25° C. of the depot precursor on addition of solvents. PC/GDO (50/50 wt/wt) is a precursor to a reversed hexagonal $H_{II}$ phase and PC/GDO (40/60 wt/wt) is a precursor to a reversed cubic $I_2$ phase;

Figure 5:
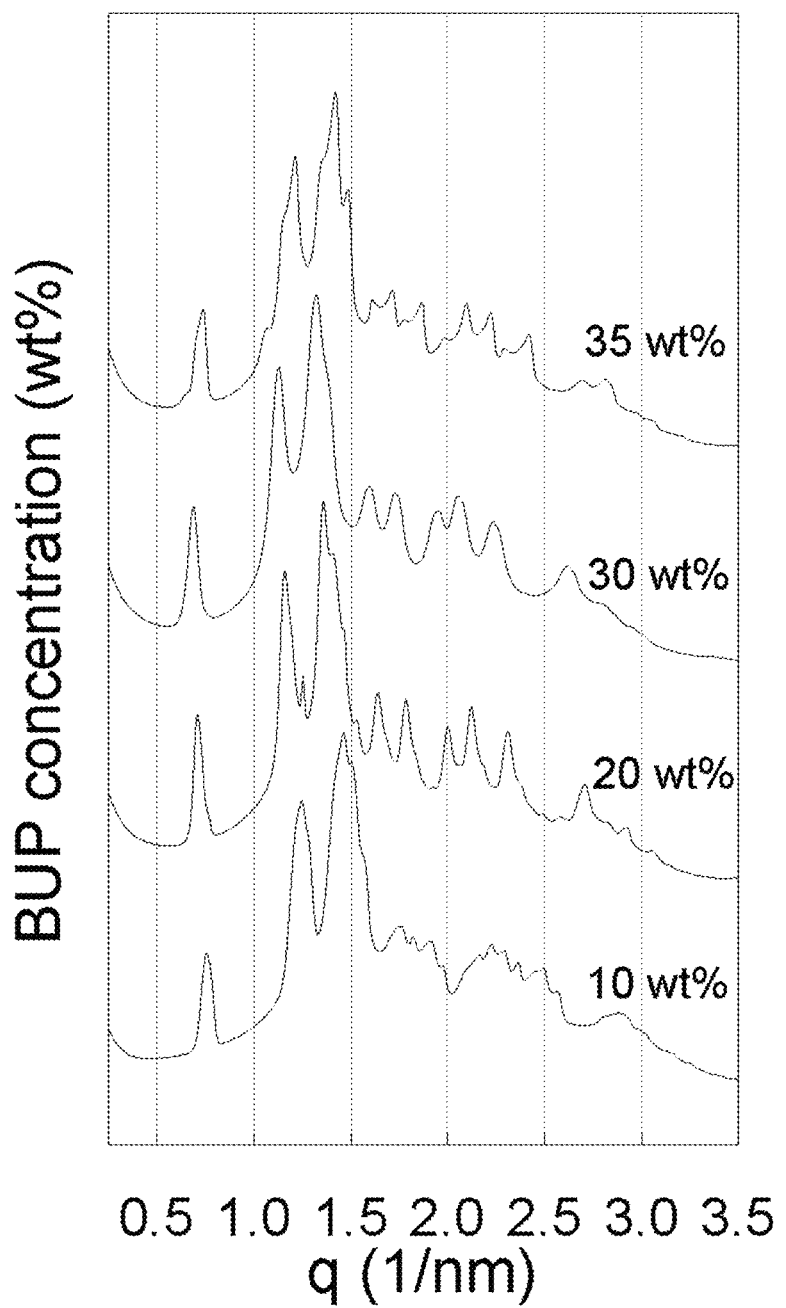
Figure 6:
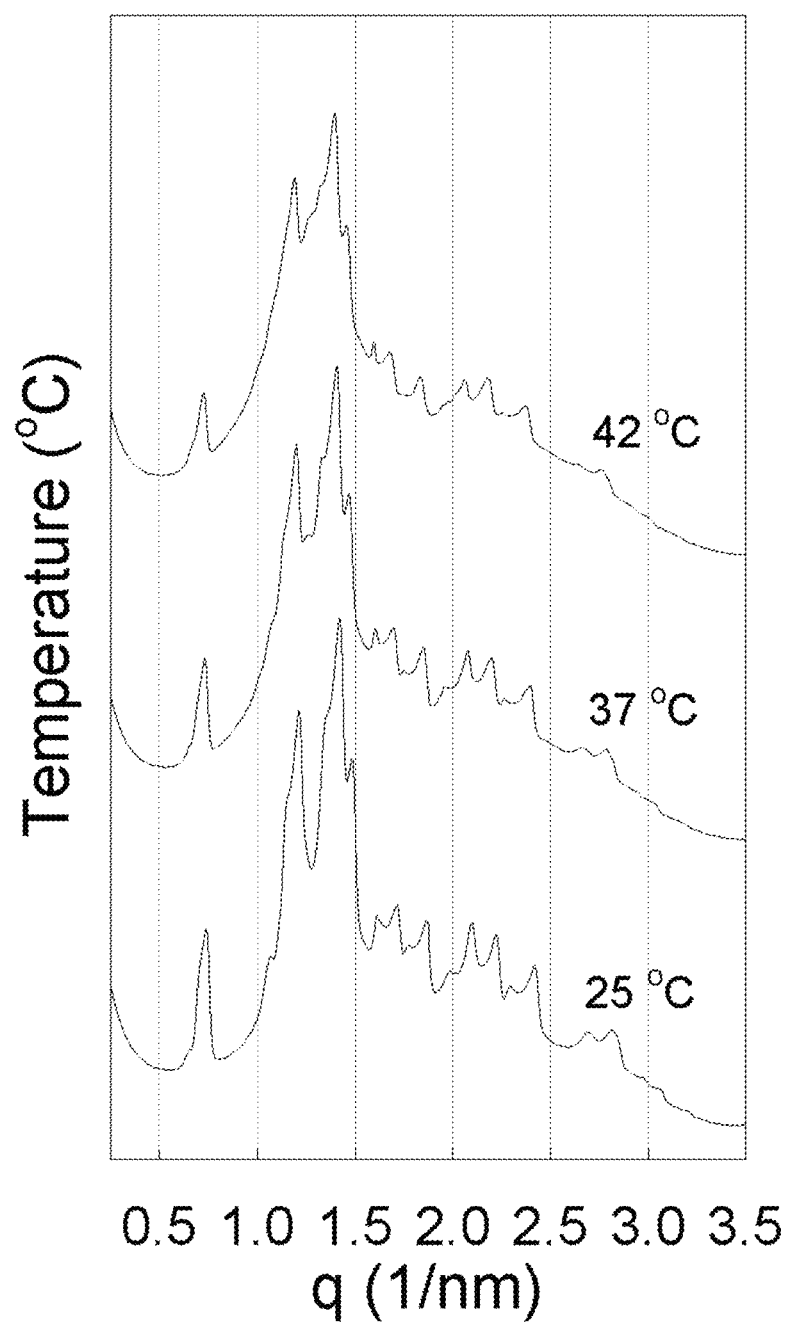
Figure 7:
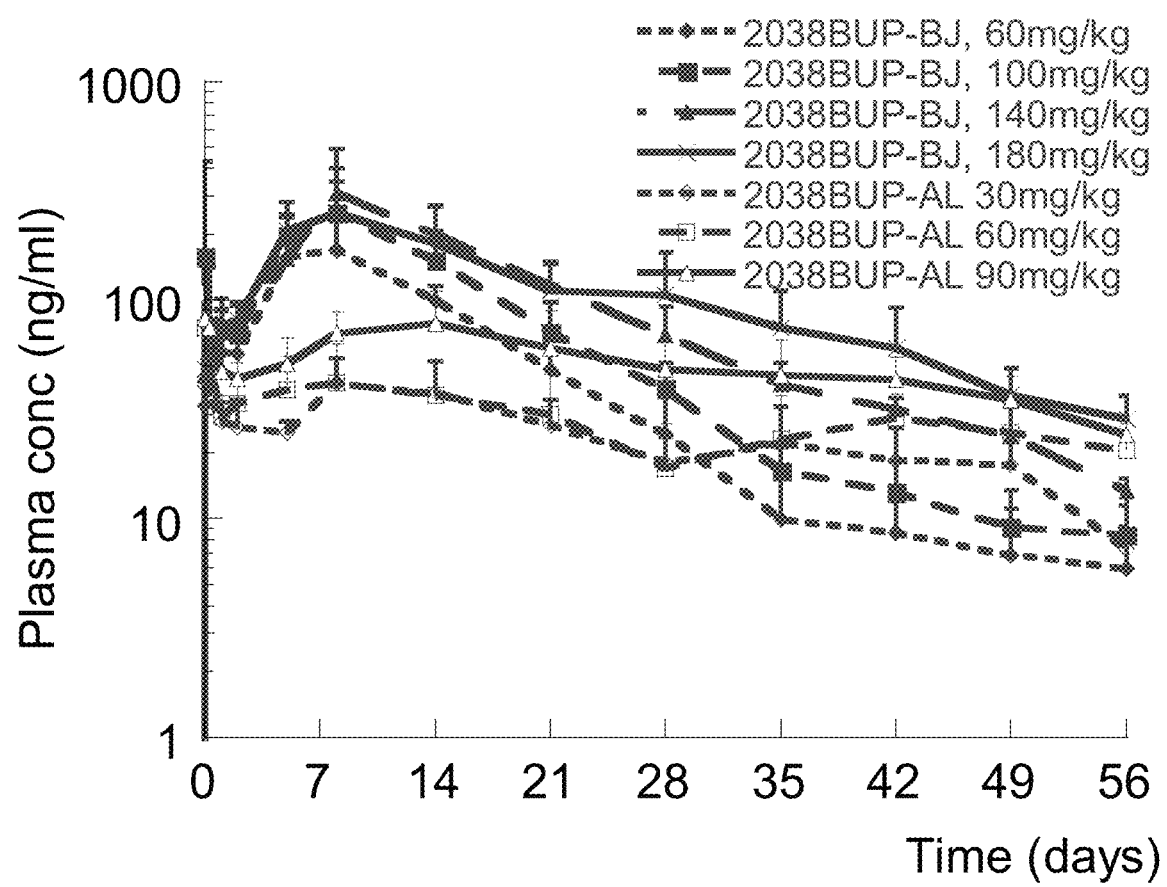
Figure 8:
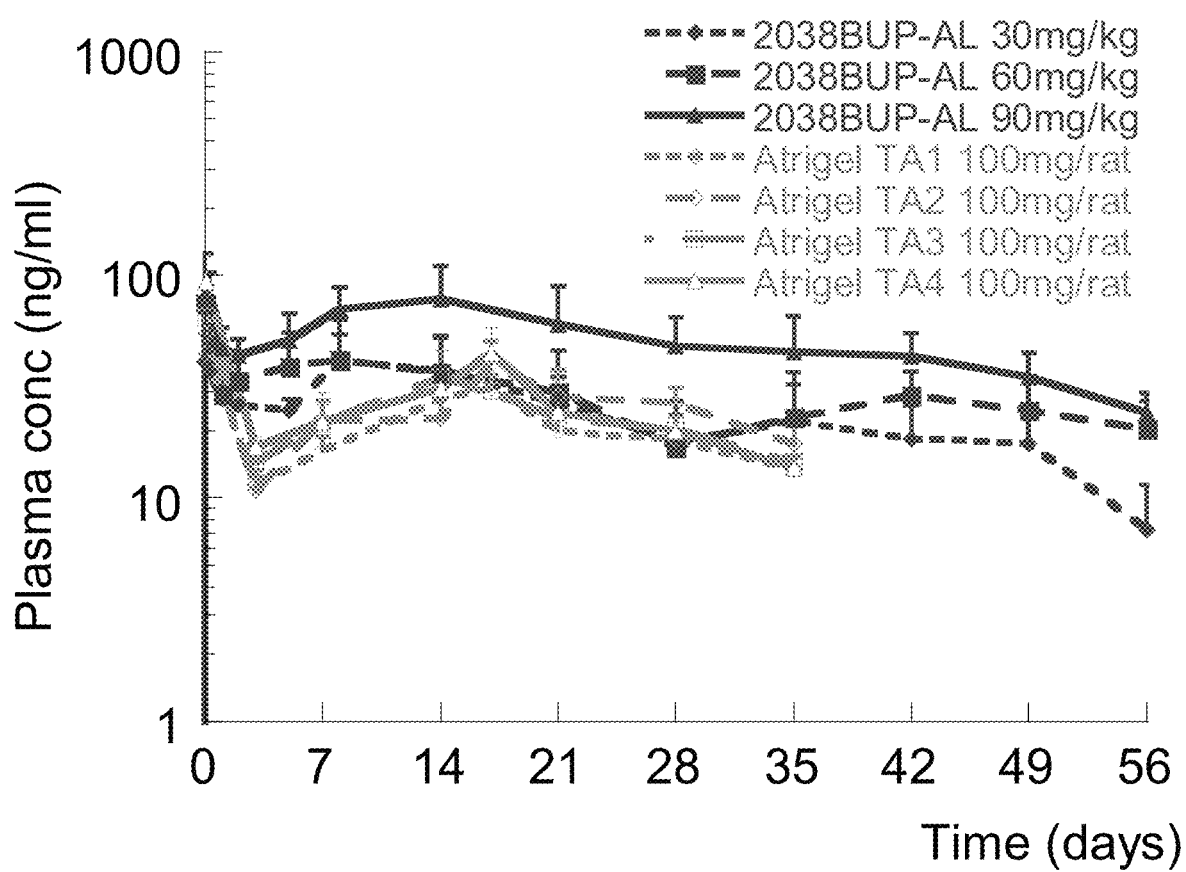
Figure 9:
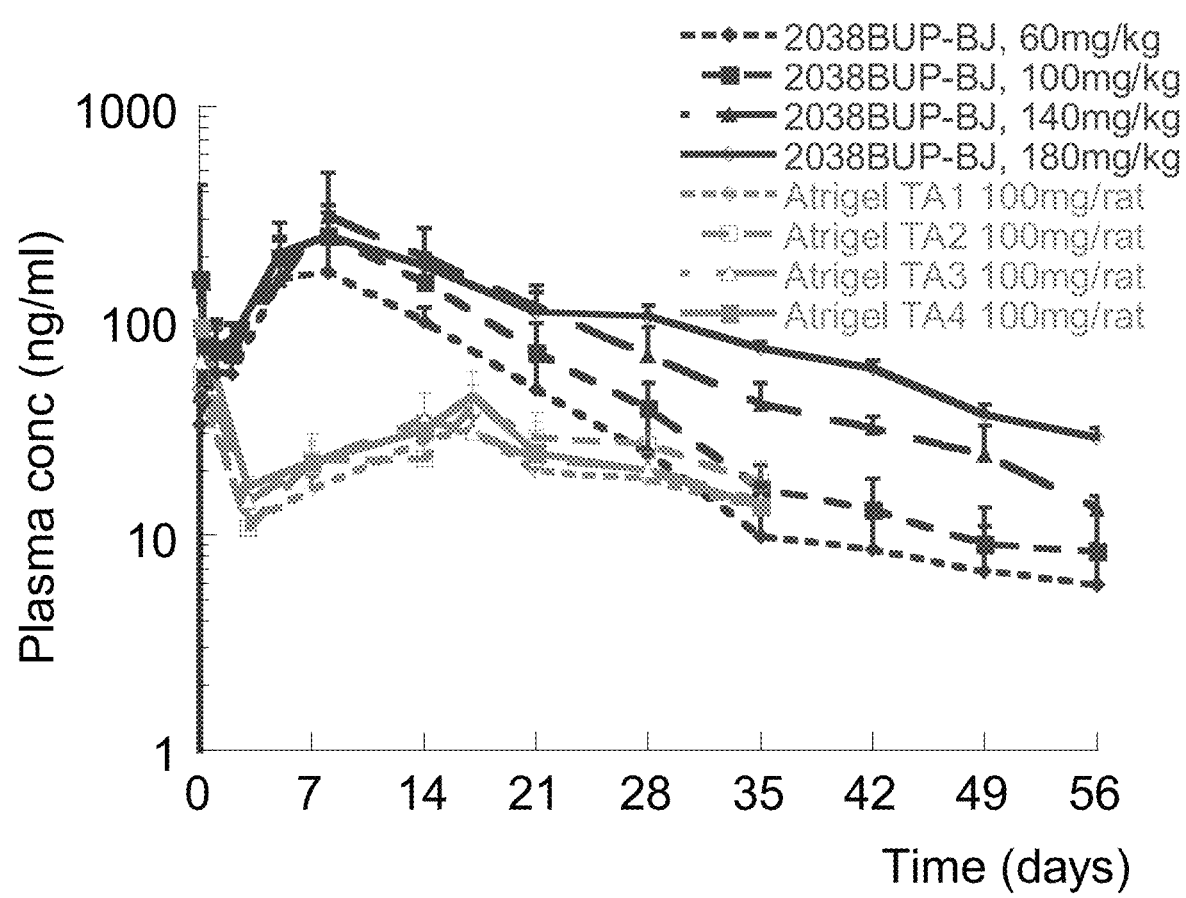
Figure 10:
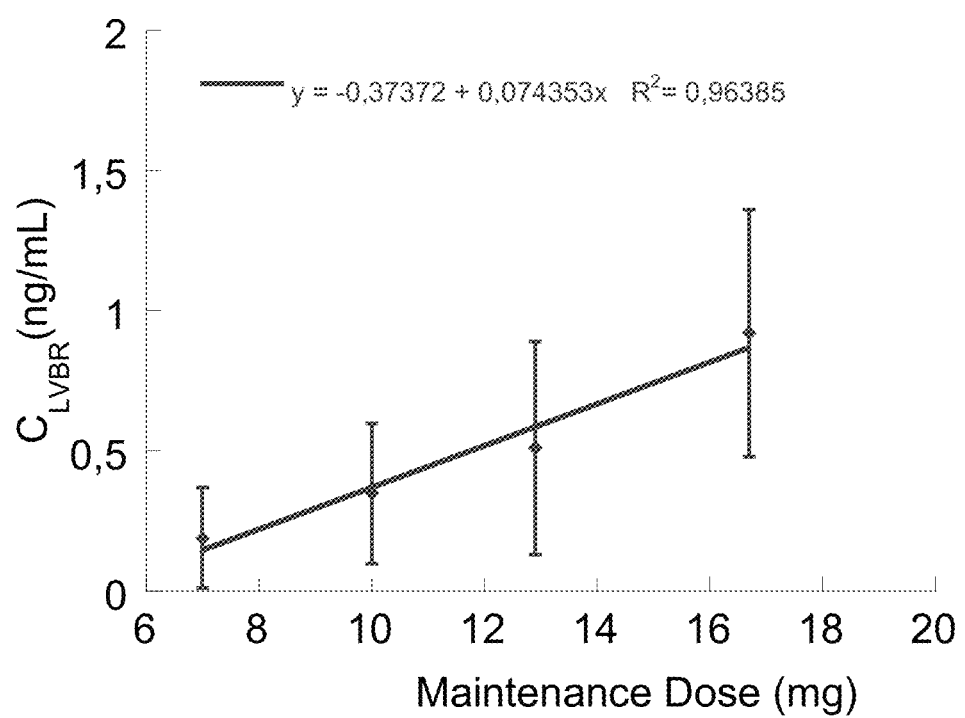

FIG. 5 shows X-ray diffractograms of the BJ formulations in PBS containing different amounts of BUP. Samples are prepared at formulation to PBS weight ratio of 1/9. Upon increasing BUP concentration the Fd3m liquid crystalline structure remains unchanged;

FIG. 6 shows X-ray diffractograms of the BJ formulation containing 35 wt % of BUP as a function of temperature. Sample is prepared at formulation to PBS weight ratio of 1/9. Upon increasing temperature from 25 to 42° C. the Fd3m liquid crystalline structure remains unchanged;

FIG. 7 shows plasma concentration of BUP following administration of lipid (solid point markers) and PLGA (open point markers) depot precursor formulations of the present invention at various concentrations;

FIG. 8 shows a comparison of Buprenorphine release in ready-to-administer polymeric compositions of Example 17 (closed markers) with previous compositions of PCT/GB2011/051057 (open markers);

FIG. 9 shows a comparison of Buprenorphine release in ready-to-administer lipid compositions of Example 17 (solid markers) with previous compositions of PCT/GB2011/051057 (open markers);

FIG. 10—Blood plasma concentration at which rescue buprenorphine was requested following depot administration plotted against the subject's previous daily maintenance dose prior to transfer to depot administration.

EXAMPLES

Example 1

Availability of Various Liquid Crystalline Phases in the Depot by Choice of Composition Injectable formulations containing different proportions of phosphatidyl choline ("PC"—Epikuron 200) and glycerol dioleate (GDO) and with EtOH as solvent were prepared to illustrate that various liquid crystalline phases can be accessed after equilibrating the depot precursor formulation with excess water.

Appropriate amounts of PC and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

Phase behaviour of PC/GDO formulations.

| Formulation | PC (wt %) | GDO (wt %) | EtOH (wt %) | Phase in $H_2O$ |
|---|---|---|---|---|
| A | 22.5 | 67.5 | 10.0 | $L_2$ |
| B | 28.8 | 61.2 | 10.0 | $I_2$ |
| C | 45.0 | 45.0 | 10.0 | $H_{II}$ |
| D | 63.0 | 27.0 | 10.0 | $H_{II}/L_\alpha$ |

$L_2$ = reversed micellar phase
$I_2$ = reversed cubic liquid crystalline phase
$H_{II}$ = reversed hexagonal liquid crystalline phase
$L_\alpha$ = lamellar phase Example 2

In Vitro Release of a Water-Soluble Substance

A water-soluble colorant, methylene blue (MB) was dispersed in formulation C (see Example 1) to a concentration of 11 mg/g formulation. When 0.5 g of the formulation was injected in 100 ml water a stiff reversed hexagonal $H_{II}$ phase was formed. The absorbency of MB released to the aqueous phase was followed at 664 nm over a period of 10 days. The release study was performed in an Erlenmeyer flask at 37° C. and with low magnetic stirring.

Figure 1:
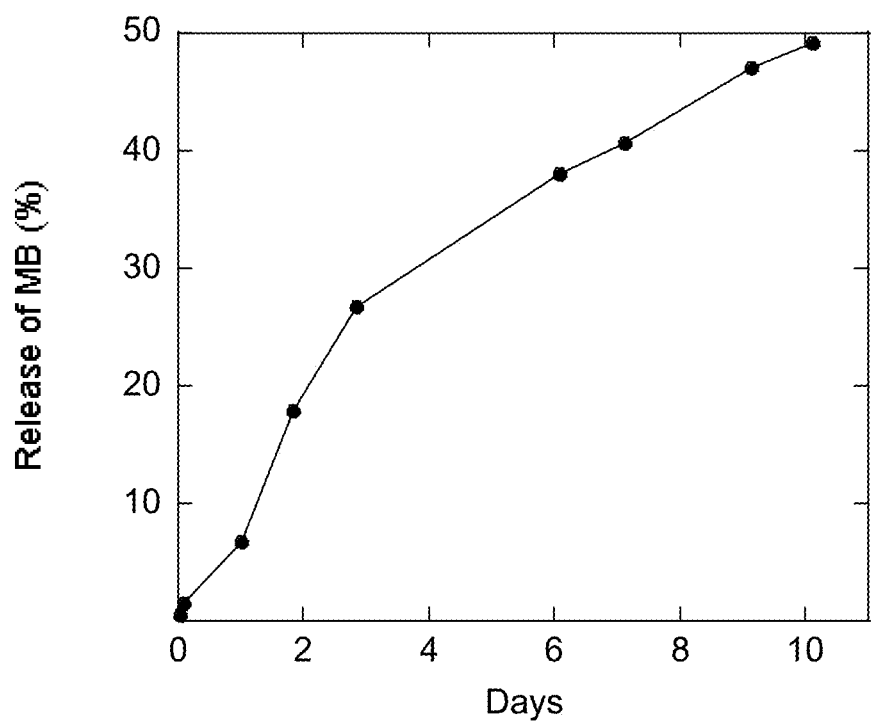

The release profile of MB (see FIG. 1) from the hexagonal phase indicates that this (and similar) formulations are promising depot systems. Furthermore, the formulation seems to give a low initial burst, and the release profile indicates that the substance can be released for several weeks; only about 50% of MB is released after 10 days.

Example 3

Viscosity in PC/GDO (5:5) or PC/GDO (4:6) on Addition of Solvent (EtOH, PG and NMP)

A mixture of PC/GDO/EtOH with approximately 25% EtOH was manufactured according to the method in Example 1. All, or nearly all, of the EtOH was removed from the mixture with a rotary evaporator (vacuum, 40° C. for 1 h followed by 50° C. for 2 h) and the resulting mixture was weighed in glass vial after which 1, 3, 5, 10 or 20% of a solvent (EtOH, propylene glycol (PG) or n-methyl pyrrolidone (NMP)) was added. The samples were allowed to equilibrate several days before the viscosity was measured with a CarriMed CSL 100 rheometer equipped with automatic gap setting.

Figure 2:
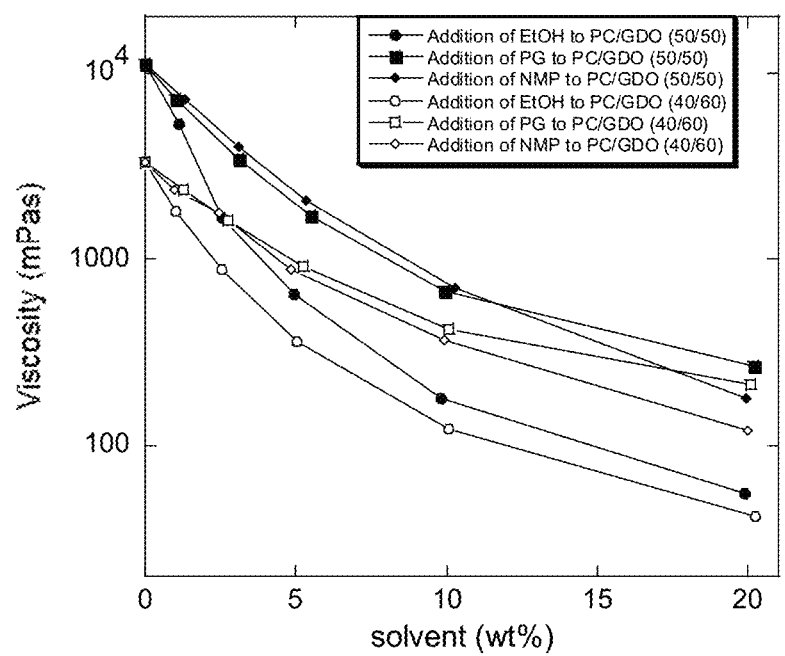
Figure 3:
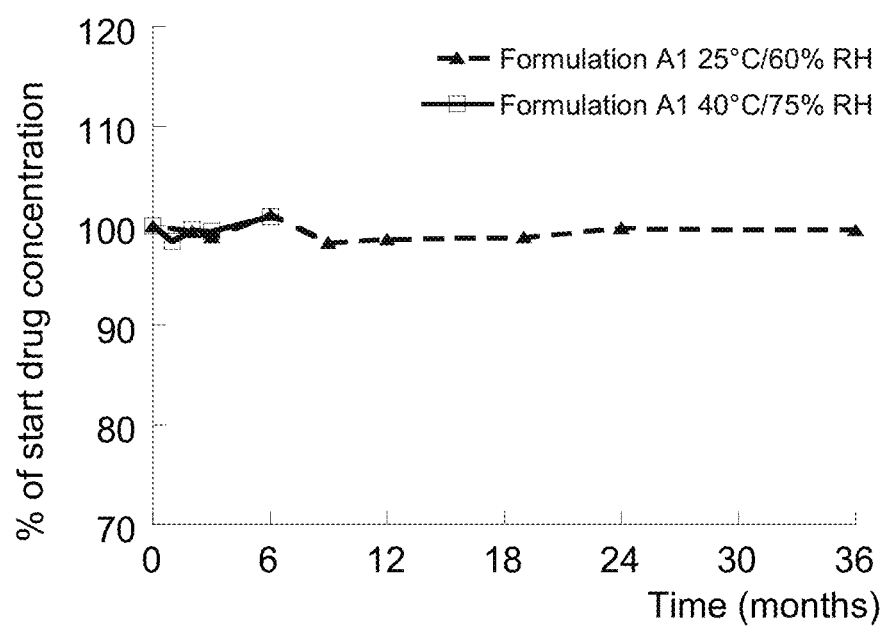
FIG. 3 shows stability of buprenorphine at long-term 25° C./60% RH and accelerated 40° C./75% RH conditions in Formulation A1 (also referred to as CAM2038) as described in Example 16.

This example clearly illustrates the need for solvent with certain depot precursors in order to obtain an injectable formulation (see FIG. 2). The viscosity of solvent-free PC/GDO mixtures increases with increasing ratio of PC. Systems with low PC/GDO ratio (more GDO) are injectable with a lower concentration of solvent.

Example 4

Preparation of Depot Precursor Compositions with Various Solvents.

Depending on composition of the formulation and the nature and concentration of active substance certain solvents may be preferable.

Depot precursor formulations (PC/GDO/solvent (36/54/10)) were prepared by with various solvents; NMP, PG, PEG400, glycerol/EtOH (90/10) by the method of Example 1. All depot precursor compositions were homogeneous one phase solutions with a viscosity that enabled injection through a syringe (23G—i.e. 23 gauge needle; 0.6 mm×30 mm). After injecting formulation precursors into excess water a liquid crystalline phase in the form of a high viscous monolith rapidly formed with NMP and PG containing precursors. The liquid crystalline phase had a reversed cubic micellar ($I_2$) structure. With PEG400, glycerol/EtOH (90/10) the viscosification/solidification process was much slower and initially the liquid precursor transformed to a soft somewhat sticky piece. The difference in appearance probably reflects the slower dissolution of PEG400 and glycerol towards the excess aqueous phase as compared to that of EtOH, NMP and PG.

Example 5

Robustness of the Behaviour of the Formulation Against Variations in the Excipient Quality.

Depot precursor formulations were prepared with several different GDO qualities (supplied by Danisco, Denmark), Table 2, using the method of Example 1. The final depot precursors contained 36% wt PC, 54% wt GDO, and 10% wt EtOH. The appearance of the depot precursors was insensitive to variation in the quality used, and after contact with excess water a monolith was formed with a reversed micellar cubic phase behaviour ($I_2$ structure).

TABLE 2

Tested qualities of GDO.

| GDO quality | Monoglyceride (% wt) | Diglyceride (% wt) | Triglyceride (% wt) |
|---|---|---|---|
| A | 10.9 | 87.5 | 1.6 |
| B | 4.8 | 93.6 | 1.6 |
| C | 1.0 | 97.3 | 1.7 |
| D | 10.1 | 80.8 | 10.1 |
| E | 2.9 | 88.9 | 8.2 |
| F | 0.9 | 89.0 | 10.1 |

Example 6

Degradation of Depot Formulation in the Rat.

Various volumes (1, 2, 6 ml/kg) of the depot precursor (36% wt PC, 54% wt GDO, and 10% wt EtOH) were injected in the rat and were removed again after a period of 14 days. It was found that substantial amounts of the formulations were still present subcutaneously in the rat after this time, see Table 3.

TABLE 3

Mean diameter of depot monolith.

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 7

Compositions Containing PC and Tocopherol.

Depot precursor formulations were prepared with several different PC/α-tocopherol compositions using the method of Example 1 (PC was first dissolved in the appropriate amount of EtOH and thereafter α-tocopherol was added to give clear homogenous solutions).

Each formulation was injected in a vial and equilibrated with excess water. The phase behaviour was evaluated visually and between crossed polarizes at 25° C. Results are presented in Table 4.

TABLE 4

Phase behaviour of PC/α-tocopherol formulations.

| α-tocopherol | PC | Ethanol | Phase in excess $H_2O$ |
|---|---|---|---|
| 2.25 g | 2.25 g | 0.5 g | $H_{II}$ |
| 2.7 g | 1.8 g | 0.5 g | $H_{II}/I_2$ |
| 3.15 g | 1.35 g | 0.5 g | $I_2$ |
| 3.6 g | 0.9 g | 0.5 g | $I_2/L_2$ |

Example 8

In Vitro Release of Water-Soluble Disodium Fluorescein.

A water-soluble colorant, disodium fluorescein (Fluo), was dissolved in a formulation containing PC/α-tocopherol/Ethanol (27/63/10 wt %) to a concentration of 5 mg Fluo/g formulation. When 0.1 g of the formulation was injected in 2 ml of phosphate buffered saline (PBS) a reversed micellar ($I_2$) phase was formed. The absorbency of Fluo released to the aqueous phase was followed at 490 nm over a period of 3 days. The release study was performed in a 3 mL vial capped with an aluminium fully tear off cap at 37° C. The vial was placed on a shaking table at 150 rpm.

The release of Fluo from the PC/α-tocopherol formulation (see Table 5) indicates that this (and similar) formulations are promising depot systems. Furthermore, the absence of a burst effect is noteworthy, and the release indicates that the substance can be released for several weeks to months; only about 0.4% of Fluo is released after 3 days.

TABLE 5

In vitro release of disodium fluorescein from PC/α-tocopherol composition.

| | % release (37° C.) | |
|---|---|---|
| Formulation | 24 h | 72 h |
| PC/α-tocopherol/EtOH: 27/63/10 wt % | <0.1* | 0.43 |

*Release below detection limit of the absorbance assay

Example 9

Solubility of Buprenorphine in Depot Precursor Formulations.

Buprenorpine solubility in formulation precursors was determined by the following protocol; buprenorphine in excess was added to formulation precursors and samples were equilibrated by end-over-end mixing at ambient room temperature for four days. Excess buprenorphine was removed by filtration and the concentration in precursor formulations was determined with HPLC. Formulation precursors in the table below differ by the additional solvent (ethanol (EtOH), benzyl alcohol (BzOH), polyethyleneglycol 400 (PEG400), benzyl benzoate (BzB), and dimethylsulphoxide (DMSO)).

TABLE 6

Buprenorphine solubility in various precursor formulations.

| Sample | SPC/ wt % | GDO/ wt % | EtOH/ wt % | Additional solvent/wt % | Buprenorphine solubility/wt % |
|---|---|---|---|---|---|
| 1 | 47.5 | 47.5 | 5 | — | 10.4 |
| 2 | 45 | 45 | 5 | EtOH/5 | 10.3 |
| 3 | 45 | 45 | 5 | BzOH/5 | 9.9 |
| 4 | 45 | 45 | 5 | PEG400/5 | 10.8 |
| 5 | 45 | 45 | 5 | BzB/5 | 11.2 |
| 6 | 45 | 45 | 5 | DMSO/5 | 15.2 |

Example 10

In Vitro Behaviour of Buprenorphine Depot Precursor Formulations.

After injection into excess water or excess saline (0.9% NaCl) a liquid crystalline phase in the form of a high viscous monolith formed with all formulation precursors described in Example 14. In general the transformation was somewhat slower with additional solvent, while buprenorphine appeared not to have a strong influence on the monolith formation.

Example 11

Ready-to-Administer Lipid Formulations

The formulations indicated in Table 7 below comprising buprenorphine, lipids and solvent were generated by adding the respective component in the required proportions to sterile injection glass vials followed by capping with sterile rubber stoppers and aluminium crimp caps. Mixing of the formulations (sample sizes 5-10 g) was performed by placing the vials on a roller mixer at ambient room temperature until liquid and homogenous formulations were obtained. The formulations were finally sterile filtered through 0.22 µm PVDF membrane filters using ca 2.5 bar nitrogen pressure.

The lipids used were Lipoid 5100 (SPC) from Lipoid, Germany, and Rylo DG19 Pharma (GDO) from Danisco, Denmark.

TABLE 7

Ready-to-administer lipid buprenorphine compositions (wt %).

| Formulation name | BUP | SPC | GDO | EtOH | NMP |
|---|---|---|---|---|---|
| A1 | 5.29 | 42.36 | 42.36 | 10.00 | — |
| A2 | 7.93 | 41.04 | 41.04 | 10.00 | — |
| A3 | 5.29 | 44.10 | 44.10 | 6.50 | — |
| A4 | 7.81 | 43.60 | 43.60 | 5.00 | — |
| A5 | 7.93 | 49.25 | 32.83 | 10.00 | — |
| A6 | 7.93 | 32.83 | 49.25 | 10.00 | — |
| A7 | 7.93 | 38.54 | 38.54 | 15.00 | — |
| A8 | 7.93 | 36.04 | 36.04 | 20.00 | — |
| A9 | 5.29 | 33.88 | 50.83 | 10.00 | — |
| A10 | 5.29 | 46.59 | 38.12 | 10.00 | — |
| A11 | 5.29 | 50.83 | 33.88 | 10.00 | — |
| A12 | 0.53 | 44.74 | 44.74 | 10.00 | — |
| A13 | 1.06 | 44.47 | 44.47 | 10.00 | — |
| A14 | 2.11 | 43.94 | 43.94 | 10.00 | — |

TABLE 7-continued

Ready-to-administer lipid buprenorphine compositions (wt %).

| Formulation name | BUP | SPC | GDO | EtOH | NMP |
|---|---|---|---|---|---|
| A15 | 15.0 | 37.5 | 37.5 | — | 10.0 |
| A16 | 15.0 | 32.5 | 32.5 | — | 20.0 |
| A17 | 35.0 | 17.5 | 17.5 | — | 30.0 |
| A18 | 35.0 | 14.0 | 21.0 | — | 30.0 |
| A19 | 15.0 | 35.0 | 35.0 | — | 15.0 |
| A20 | 15.0 | 30.0 | 30.0 | — | 25.0 |
| A21 | 30.0 | 25.0 | 25.0 | — | 20.0 |
| A22 | 40.0 | 12.0 | 18.0 | — | 30.0 |
| A23 | 30.0 | 16.0 | 24.0 | — | 30.0 |
| A24 | 25.0 | 22.0 | 33.0 | — | 30.0 |
| A25 | 15.0 | 32.5 | 32.5 | 5.0 | 15.0 |

Example 12

Ready-to-Administer Polymer Formulations

The formulations indicated in Table 8 below comprising buprenorphine, polymer and solvent were generated by adding the respective component in the required proportions to a sterile injection glass vial followed by capping with sterile rubber stopper and aluminium crimp cap. Mixing of the formulations (sample sizes 5-10 g) was performed by placing the vials on a roller mixer at ambient room temperature until liquid and homogenous formulations were obtained. The formulations were finally sterile filtered through 0.22 µm PVDF membrane filters using ca 2.5 bar nitrogen pressure.

The polymer used was PLGA (polymer type 50/50 Poly (DL-lactide-co-glycolide) with inherent viscosity 0.59 dL/g) from Birmingham Polymers Inc., USA.

TABLE 8

Ready-to-administer polymer buprenorphine compositions (wt %).

| Formulation name | BUP | PLGA | NMP |
|---|---|---|---|
| B1 | 15.0 | 21.25 | 63.75 |
| B2 | 20.0 | 20.00 | 60.00 |
| B3 | 25.0 | 18.75 | 56.25 |
| B4 | 32.5 | 16.9 | 50.6 |
| B5 | 35.0 | 16.2 | 48.8 |
| B6 | 40.0 | 15.0 | 45.0 |

Example 13

Formulations Comprising Water and Buprenorphine Salts

The formulations indicated in Table 9 below comprising buprenorphine, lipids and solvent were generated as described in Example 16 above. For the formulations comprising water, the additives hydrochloric acid (HCl) and citric acid (CA) were first dissolved in the aqueous phase followed by addition to the other components. The respective buprenorphine salt forms (i.e., hydrochloride, citrate, benzoate and pamoate salts) are generated in the formulations after mixing of all components.

The lipids used were Lipoid 5100 (SPC) from Lipoid, Germany, and Rylo DG19 Pharma (GDO) from Danisco, Denmark. Benzoic acid and pamoic (or embonic) acid are abbreviated Bz and PAM, respectively.

TABLE 9

Ready-to-administer lipid buprenorphine compositions comprising water and buprenorphine salts (wt %).

| Formulation name | BUP | SPC | GDO | EtOH | NMP | HCl(aq) pH 0.52 | WFI | CA | Bz | PAM |
|---|---|---|---|---|---|---|---|---|---|---|
| C1 | 2.11 | 33.95 | 33.95 | 15.00 | — | 15.00 | — | — | — | — |
| C2 | 5.29 | 31.86 | 31.86 | 15.00 | — | — | 15.00 | 1.00 | — | — |
| C3 | 1.06 | 33.97 | 33.97 | 15.00 | — | — | 15.00 | 1.00 | — | — |
| C4 | 2.11 | 32.95 | 32.95 | 15.00 | — | — | 15.00 | 2.00 | — | — |
| C5 | 2.11 | 33.75 | 33.75 | 15.00 | — | — | 15.00 | 0.40 | — | — |
| C6 | 2.11 | 38.75 | 38.75 | 10.00 | — | — | 10.00 | 0.40 | — | — |
| C7 | 5.29 | 41.10 | 41.10 | 10.00 | — | — | — | — | 2.60 | — |
| C8 | 5.29 | 35.16 | 35.16 | 5.00 | 15.00 | — | — | — | — | 4.39 |
| C9 | 5.29 | 35.71 | 35.71 | 5.00 | 15.00 | — | — | — | — | 3.29 |
| C10 | 5.29 | 36.26 | 36.26 | 5.00 | 15.00 | — | — | — | — | 2.19 |
| C11 | 1.06 | 34.47 | 34.47 | 15.00 | — | — | 15.00 | — | — | — |
| C12 | 2.11 | 33.95 | 33.95 | 15.00 | — | — | 15.00 | — | — | — |
| C13 | 1.06 | 39.47 | 39.47 | 10.00 | — | — | 10.00 | — | — | — |

Example 14

Lipid Buprenorphine Formulation Filled into Pre-Filled Syringes.

Formulation A1, hereinafter referred to as CAM2038, was manufactured according to Example 11 above at a batch size of 100 mL. The formulation was filled into 1 mL (long) pre-filled syringes (1.0 mL long Gerresheimer glass, staked needle 25G 16 mm thin wall, oily siliconized, batch no: 1000102210) and plunger stoppers (West 2340 4432/50/GRAU B240 Westar® RS, lot. Nr: 1112020528) and plunger rods (Gerresheimer Plunger rod 1 mL long 55103, art no: 551030001) were assembled.

Example 15

Controlling PK Profile by Composition

Figure 4:
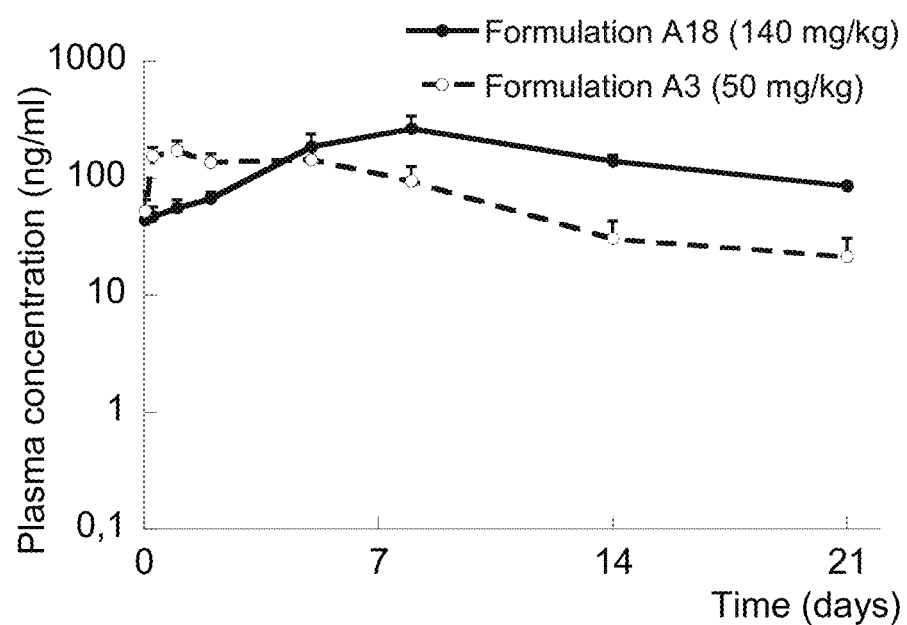
FIG. 4 shows plasma profiles in rats (N=6) after subcutaneous injection of Formulation A18 and A3 (Example 11) at doses of 140 mg/kg and 50 mg/kg, respectively.

Formulations A3 and A18 (see Example 11) were administered subcutaneously to rats in doses of 50 and 140 mg/kg, respectively (N=6 per group). Blood samples were collected up to 21 days after dosing. The plasma concentrations were determined as described below and the respective pharmacokinetic profiles are shown in FIG. 4. As can be seen, whereas Formulation A3 provides a short time to Cmax (about 24 hrs) and thereafter stable and slowly declining plasma levels, Formulation A1b provides a longer time to Cmax (ca 8 days) and thereafter slowly declining plasma levels. It is also noteworthy that despite the high buprenorphine load of 35 wt % in Formulation A18 and the higher dose administered, the plasma levels over the first days are lower compared to Formulation A3.

Protocol:

The formulation A3/A18 was administered subcutaneously to rats in doses of 50 and 140 mg/kg respectively and blood samples were collected pre-dose, 1 hrs, 6 hrs, 1 day, 2 days, 5 days, 8 days and 14 days after dosing. In a separate group, Temgesic (aqueous injection solution of buprenorphine hydrochloride with an equivalent buprenorphine base concentration of 0.30 mg/mL) was administered intravenously (0.45 mg/kg, N=6) and blood samples were collected pre-dose, 1 min, 5 min, 10 min, 30 min, 60 min, 3 hrs, 6 hrs and 24 hrs. The plasma concentrations were determined with the aid of a commercial ELISA kit adapted for analysis of buprenorphine in rat plasma. The area-under-the-curve (AUC) for the respective treatment groups was calculated and the absolute bioavailability was calculated by comparing the AUC for the subcutaneous Formulation A3 dose groups with the AUC for the Temgesic intravenous dose group. The results revealed very high absolute bioavailability for all Formulations.

Example 16

The lipid liquid crystalline phase structure of hydrated formulations containing high concentration buprenorphine was studied by synchrotron SAXD. Diffractograms were recorded at the I9-11-4 SAXS beamline (MAX-lab, Lund University). Herein, synchrotron SAXS is used to study the effect of BUP concentration on the liquid crystalline (LC) phase structure for 40/60 SPC/GDO and 70/30 (Lipid+BUP)/NMP ("BJ"). Temperature effect on the LC phase structure containing 35 wt % of BUP was also studied at 25, 37 and 42° C. to cover the relevant temperature range.

Material

TABLE 10

Excipients used in the experiment.

| Explanation | Abbreviation | Delivered by |
|---|---|---|
| Soy phosphatidylcholine | SPC | Lipoid |
| Glycerol dioleate (Rylo DG 19) | GDO | Danisco |
| N-Methyl-2-pyrrolidone | NMP | ISP |
| Phosphate buffered saline | PBS | Sigma-Aldrich |
| Sterile water | H2O | Apoteket |

Briefly, the lipid formulations were prepared by weighing all components followed by mixing on a roller table at room temperature. Formulations were then equilibrated in phosphate buffered saline (PBS) at weight ratio 1/9 at room temperature for 5 days and their transparency and homogeneity were noted 3 and 4 days after hydration, respectively. Approximately 100 mg of each formulation was equilibrated with PBS buffer.

Synchrotron SAXD measurements were performed at the I9-11-4 beamline, MAX-lab. The samples were exposed to X-rays for 60 s at each of the three temperatures (25, 37 and 42° C.). The samples were allowed to equilibrate for at least 5 minutes at each temperature before the diffractograms were recorded.

Table 11 lists the composition of samples studied by SAXD. The SAXD data is shown and further discussed below.

TABLE 11

"BJ"-BUP formulations with different fraction of
BUP and PBS dilution.

| Formulation ID No: | SPC/GDO | Lipid/NMP/BUP | Formulation/PBS |
|---|---|---|---|
| 4217 | 40/60 | 69.7/30.3/0 | 1/9 |
| 4216 | 40/60 | 59.9/29.8/10.3 | 1/9 |
| 4215 | 40/60 | 49.8/30.2/20.0 | 1/9 |
| 4214 | 40/60 | 39.9/30.2/29.9 | 1/9 |
| 4213-5 | 40/60 | 34.9/30.1/35.0 | 1/9 |

Effect of BUP in Formulations

The "BJ" (high loading, 35% BUP) formulations with a 40/60 SPC/GDO and 30% NMP exhibit a cubic micellar (I2) phase (Fd3m) at all fractions of BUP (0-35%), as seen in FIG. 5. The cubic Fd3m structure is also preserved when heating from 25 to 37 and 42° C. (FIG. 6).

Conclusion

The lipid liquid crystalline phases of hydrated formulation containing BUP has been studied with synchrotron SAXS. The studies show that even up to at least 35% BUP loading, the characteristics of the desired liquid crystalline lipid phases are shown when preformulations are added to aqueous buffer (10% formulation in buffer). This phase behaviour is shown at 25° C., 37° C. and 42° C. and 35% BUP.

Example-17 High Loading PLGA and Lipid Precursor Formulations

Formulations 2038BUP-BJ (lipid—352 mg/mL BUP) and 2038UP-AL (PLGA—150 mg/mL BUP) were prepared according to the protocol of the previous Examples (16 and 12) and with the components as shown below (in wt %). Each composition was tested by subcutaneous injection into 6 rats at each of several dosage levels.

PK-12-454

| Test item | BUP | SPC | GDO | NMP |
|---|---|---|---|---|
| 2038BUP-BJ | 35.00 | 14.00 | 21.00 | 30.00 |

| Group No | No of animals | Treatment | Route of administration | Dose volume (mL/kg) | Dose of BUP (mg/kg) |
|---|---|---|---|---|---|
| 1 | 6 | 2038BUP-BJ | s.c. | 0.17 | 60 |
| 2 | 6 | 2038BUP-BJ | s.c. | 0.29 | 100 |
| 3 | 6 | 2038BUP-BJ | s.c. | 0.40 | 140 |
| 4 | 6 | 2038BUP-BJ | s.c. | 0.51 | 180 |

| Test item | BUP | PLGA | NMP |
|---|---|---|---|
| 2038BUP-AL | 15.00 | 21.25 | 63.75 |

| Group No | No of animals | Treatment | Route of administration | Dose of BUP (mg/kg) | Dose volume (mL/kg) |
|---|---|---|---|---|---|
| 1 | 6 | 2038BUP-AL | s.c. | 30 | 0.2 |
| 2 | 6 | 2038BUP-AL | s.c. | 60 | 0.4 |
| 3 | 6 | 2038BUP-AL | s.c. | 90 | 0.6 |

FIG. 7 shows the results of plasma BUP measurements for several weeks following administration of the two compositions. It is notable that:

The lipid formulation shows a gently tapering profile over the study period

The lipid formulation shows a plasma level at the 28-day re-administration point which depends directly and approximately proportionally upon the administered dose.

The PLGA formulation shows a flatter profile with lower total AUC during the study period.

The PLGA formulation is apparently less dose proportional, with the 30 mg and 60 mg doses providing the same plasma profile for the first month.

For comparison, the precursor formulations of the present invention were plotted against the data provided in PCT/GB2011/051057 relating to the following compositions:

TA 1: 15% Buprenorphine base in 45% 50/50 PLGH (26 kD) and 55% NMP

TA 2: 20% Buprenorphine base in 40% 50/50 PLGH (17 kD) and 60% NMP

TA 3: 20% Bup base in 20% 50/50 PLGH (26 Kd), 20% 50/50 PLGH (12 kD) and 60% NMP TA 4: 20% Buprenorphine base in 45% 50/50 PLGH (12 kD) and 55% NMP FIG. 8 shows the comparison of the ready-to-administer compositions of the present invention with the previously known polymer depot composition of PCT/GB2011/051057. It is evident that even at much lower doses the amount of available BUP in the compositions of the present invention is greatly increased. A typical rat weighs around 330 g and thus a 60 mg/kg does equates to around 20 mg/rat but provides similar AUC availability to 100 mg/rat for the known formulation.

FIG. 9 shows the comparison of the ready-to-administer compositions of the present invention with the previously known polymer depot composition of PCT/GB2011/051057. It is evident that the AUC bioavailability, release shape and dose proportionality are all significantly better for the lipid compositions of the present invention. In particular, the lowest dose of 60 mg/kg equates to around 20 mg/rat but provides much better release profile and bioavailability than the known composition at 100 mg/rat.

The invention claimed is:

1. A pre-filled syringe containing a composition, the composition comprising:
    about 5% by weight of buprenorphine;
    about 10% by weight of ethanol;
    about 42% by weight of a phosphatidylcholine; and
    about 42% by weight of glycerol dioleate.

2. The pre-filled syringe of claim 1, wherein the pre-filled syringe contains less than 5 mL of the composition.

3. The pre-filled syringe of claim 2, wherein the pre-filled syringe contains less than 2 mL of the composition.

4. The pre-filled syringe of claim 3, wherein the pre-filled syringe contains less than 1 mL of the composition.

5. The pre-filled syringe of claim 1, wherein the composition comprises about 3 mg to about 40 mg of buprenorphine (calculated as buprenorphine free base).

6. The pre-filled syringe of claim 5, wherein the composition comprises about 5 mg to about 30 mg of buprenorphine (calculated as buprenorphine free base).

7. The pre-filled syringe of claim 1, wherein the composition has a viscosity that is about 1 to about 1000 mPas at 20° C., as measured with a CarriMed CSL 100 rheometer equipped with automatic gap setting.

8. The pre-filled syringe of claim 7, wherein the composition has a viscosity that is about 100 mPas to about 500 mPas at 20° C., as measured with a CarriMed CSL 100 rheometer equipped with automatic gap setting.

9. The pre-filled syringe of claim 1, wherein the pre-filled syringe further comprises a needle stick prevention safety device.

10. The pre-filled syringe of claim 1, wherein the pre-filled syringe further comprises an auto injector.

11. The pre-filled syringe of claim 1, wherein the pre-filled syringe is disposable.

12. The pre-filled syringe of claim 1, wherein the pre-filled syringe comprises a needle having a gauge greater than 18 G.

13. The pre-filled syringe of claim 12, wherein the pre-filled syringe comprises a needle having a gauge greater than 20 G.

14. The pre-filled syringe of claim 13, wherein the pre-filled syringe comprises a needle having a gauge greater than 22 G.

15. The pre-filled syringe of claim 14, wherein the pre-filled syringe comprises a needle having a gauge higher than 23 G.

16. The pre-filled syringe of claim 15, wherein the pre-filled syringe comprises a needle having a gauge higher than 25 G.

17. The pre-filled syringe of claim 1, wherein the pre-filled syringe has a capacity of about 1 mL.

18. The pre-filled syringe of claim 1, wherein the composition is storage stable at 25° C./60% relative humidity.

19. The pre-filled syringe of claim 1, wherein the composition is storage stable at 40° C./75% relative humidity.

20. The pre-filled syringe of claim 1, characterized in that the composition, when administered to a subject, exhibits a variation between Cmin and Cmax of buprenorphine at steady-state administration that is between 0.4 ng/mL and 10 ng/mL.

21. The pre-filled syringe of claim 20, characterized in that the composition, when administered to a subject, exhibits a variation between Cmin and Cmax of buprenorphine at steady-state administration that is between 0.5 ng/mL and 8 ng/mL.

22. The pre-filled syringe of claim 1, characterized in that the composition, when administered to a subject, provides a Cmax of buprenorphine of no more than 0.3 ng/mL per mg of administered buprenorphine after a single administration.

23. The pre-filled syringe of claim 1, wherein the composition, after contact with an aqueous fluid, forms a liquid crystalline phase structure.

24. The pre-filled syringe of claim 23, wherein the liquid crystalline phase structure is a non-lamellar crystalline phase structure.

25. A pre-filled syringe containing a composition, the composition comprising:
 about 5.29% by weight of buprenorphine;
 about 10% by weight of ethanol;
 about 42.36% by weight of a phosphatidylcholine; and
 about 42.36% by weight of glycerol dioleate.

26. The pre-filled syringe of claim 25, wherein the pre-filled syringe contains less than 1 mL of the composition.

27. The pre-filled syringe of claim 25, wherein the composition comprises about 3 mg to about 40 mg of buprenorphine (calculated as buprenorphine free base).

28. The pre-filled syringe of claim 27, wherein the composition comprises about 5 mg to about 30 mg of buprenorphine (calculated as buprenorphine free base).

29. The pre-filled syringe of claim 25, wherein the composition has a viscosity that is about 1 to about 1000 mPas at 20° C., as measured with a CarriMed CSL 100 rheometer equipped with automatic gap setting.

30. The pre-filled syringe of claim 25, wherein the pre-filled syringe is disposable.

* * * * *